(12) United States Patent
Spivey et al.

(10) Patent No.: US 7,070,920 B2
(45) Date of Patent: Jul. 4, 2006

(54) SCREENING ARRANGMENT FOR SCREENING IMMUNOASSAY TESTS AND AGGLUTINATION TESTS

(75) Inventors: Robin James Spivey, Bangor (GB); Christopher William Hand, Abingdon (GB); Dene Baldwin, Oxford (GB); Osborn Pierce Jones, Gwernafalau (GB)

(73) Assignee: Cozart Bioscience Limited, Abingdon (GB)

( * ) Notice: Subject to any disclaimer, the term of this patent is extended or adjusted under 35 U.S.C. 154(b) by 542 days.

(21) Appl. No.: 09/760,374

(22) Filed: Jan. 12, 2001

(65) Prior Publication Data

US 2001/0034068 A1 Oct. 25, 2001

Related U.S. Application Data

(63) Continuation-in-part of application No. PCT/GB99/02261, filed on Jul. 14, 1999.

(30) Foreign Application Priority Data

Jul. 14, 1998 (GB) .............................................. 9815302

(51) Int. Cl.
*G01N 33/53* (2006.01)
*G01N 33/543* (2006.01)

(52) U.S. Cl. ................................ 435/4; 435/6; 435/7.1; 435/7.9; 435/7.92; 435/287.1; 435/287.2; 435/287.3; 435/805; 435/810; 435/970; 436/164; 436/172; 436/518; 436/524; 436/528; 436/532; 436/805; 422/68.1; 422/82.01; 356/73; 356/246; 356/317; 356/318; 356/338; 356/343; 356/417; 356/445; 356/446

(58) Field of Classification Search .................... 435/4, 435/6, 7.1, 7.9, 7.92, 287.1–287.3, 805, 810, 435/970; 436/164, 172, 518, 524, 528, 532, 436/805, 810; 422/68.1, 82.01; 356/73, 318, 356/445, 446, 246, 317, 338, 343, 417
See application file for complete search history.

(56) References Cited

U.S. PATENT DOCUMENTS 4,521,522 A 6/1985 Lundström et al.
(Continued)

FOREIGN PATENT DOCUMENTS

EP 0 291 194 11/1988
(Continued)

OTHER PUBLICATIONS

Brecht, A. and R. Abuknesha, "Multi–analyte immunoassays application to enviromental analysis", *trends in analytical chemistry*, vol. 14, No. 7, 1995, pp. 361–371.
(Continued)

*Primary Examiner*—Chris Chin
*Assistant Examiner*—Kartic Padmanabhan
(74) *Attorney, Agent, or Firm*—Flynn, Thiel, Boutell & Tanis, P.C.

(57) ABSTRACT

A screening device for performing an immunoassay test to detect the presence of a compound in a body fluid. The device includes a holder for removably receiving a membrane to which the fluid has been applied. A light is directed to the membrane. A photodetector measures the concentration of the light reflected back from the membrane. Specifically, the concentrations of reflected light from a control zone and a test zone are measured. Signals representative of the measured light concentrations are applied to a processor. If a specified concentration of predetermined light from a control zone on the membrane is detected, the processor considers the test to be successful. In the test is successful, the processor, based upon the measured concentration of reflected light from the test zone, generates data representative of the presence of the compound.

13 Claims, 16 Drawing Sheets

U.S. PATENT DOCUMENTS

| | | | |
|---|---|---|---|
| 4,676,653 A | | 6/1987 | Strohmeier et al. |
| 5,313,264 A | * | 5/1994 | Ivarsson et al. ............... 356/73 |
| 5,393,496 A | | 2/1995 | Seymour |
| 5,408,535 A | | 4/1995 | Howard, III et al. |
| 5,559,041 A | | 9/1996 | Kang et al. |
| 5,580,794 A | | 12/1996 | Allen |
| 5,633,724 A | | 5/1997 | King et al. |
| 5,639,671 A | | 6/1997 | Bogart et al. |

FOREIGN PATENT DOCUMENTS

| | | |
|---|---|---|
| EP | 0 301 583 | 2/1989 |
| EP | 0 560 410 | 9/1993 |
| EP | 0 186 799 | 10/1993 |
| EP | 0 703 454 | 3/1996 |
| GB | 2 239 314 | 6/1991 |
| GB | 2 241 329 | 8/1991 |
| WO | WO 97/31268 | 8/1997 |
| WO | WO 98/32004 | 7/1998 |

OTHER PUBLICATIONS

Patton, Wayne F., "Biologist's perspective on analytical imaging systems as applied to protein gel electrophoresis", *Journal of Chromatography* A, 698 (1995), pp. 55–87.

PCT App. No. PCT/GB99/02261, International Preliminary Examination Report, Oct., 2000.

\* cited by examiner

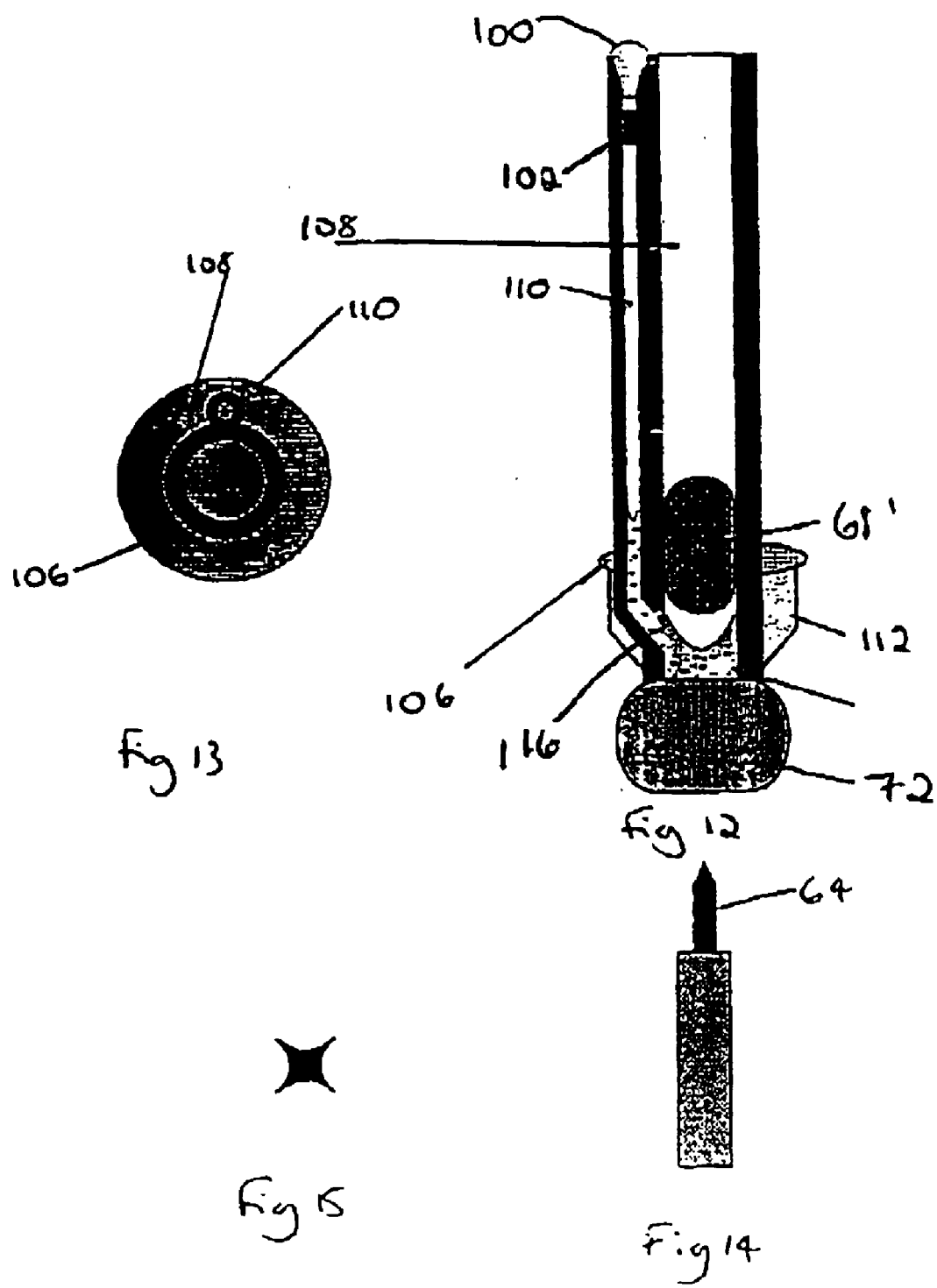

SCREENING ARRANGMENT FOR SCREENING IMMUNOASSAY TESTS AND AGGLUTINATION TESTS

RELATIONSHIP TO EARLIER FILED APPLICATION

This application is a continuation-in-part of International Application PCT/GB99/02261, publication No. WO 00/04381, with an International filing date of Jul. 14, 1999.

BACKGROUND OF THE INVENTION

This invention relates to a screening device and methods of screening immunoassay tests and agglutination tests. In particular the invention is applicable to a screening device for detecting the presence and concentration of particular drugs in a sample of saliva.

Samples of bodily fluid such as blood, sweat, urine and saliva may be used to detect the presence of particular compounds, such as drugs, in the body. Known methods of testing such samples for the presence of compounds include immunoassay "strip" testing where an antibody is labelled with a suitable marker, for example a visible marker such as colloidal gold, and drawn along a membrane passing over test regions and a control region impregnated with analyte conjugate substances or other binding substances. The presence of particular compounds in the sample are detected by a visible change occurring in the corresponding region due to the interaction of the labelled antibodies and the conjugate substances resulting in visible lines forming on the membrane in some of these regions. The colour formed may be proportional to or inversely proportional to analyte concentration depending on the assay format.

The interpretation of the lines formed by such immunoassay testing has previously been carried out subjectively by an operator comparing the intensity of the test line (or the absence or presence of a line) with that of a control, or reference, line.

U.S. Pat. No. 5,580,794 describes a disposable electronic assay device. For single analytes only one light source and detector is necessary; for two analytes, two sets of light source and detector is necessary and so on.

SUMMARY OF THE INVENTION

The invention in its various aspects is defined in the independent claims below, to which reference should now be made. Advantageous features are set forth in the appendant claims.

We have appreciated that in some fields of drug testing, for example in the use of a sample matrix other than urine such as saliva or blood, the amount of drug present in the sample may be very low, and the operator must be able to distinguish between a negative test corresponding to a complete absence of the drug in the sample and very low levels of drug present. This is difficult, requiring highly trained and skilled operators, and can prove unreliable when the levels of drugs are very low. For example, it is particularly difficult for an operator to distinguish between levels of cannabis of 6 ng/mL or lower by eye. If the test is to be run outside the laboratory, it is even more likely to be subject to inaccuracies which may be exacerbated by poor lighting conditions or by other environmental factors. We have, therefore, recognised the need for a portable drug tester which produces reliable and reproducible results.

We have also appreciated that a non-invasive test that can be conducted for example by the roadside would be beneficial. In a preferred embodiment of the invention we have therefore provided an automatic drug tester which can detect even very low levels of drugs from a saliva sample.

Preferred embodiments of the invention are described with respect to the drawings. In two of the preferred embodiments, immunoassay tests and agglutination tests run on samples of bodily fluid to detect the presence of particular compounds such as drugs in the body may be screened in the screening device. A test membrane is inserted into the screening device and illuminated. The reflected image is detected and the digitised data processed. For immunoassay tests, the digitised data is segmented and data for the tent region is compared to that from the control region and the background regions to determine whether the test data exhibits any significant results. For agglutination tests, the digitised data is processed to determine the number and size of the areas of coagulation to determine whether the test data exhibits any significant results, In another preferred embodiment, a swab for taking a bodily sample incorporates a run fluid capsule. Once an adequate sample of bodily fluid has been collected and the swab is placed in contact with the test membrane, the run fluid capsule is pierced by a spike provided on the swab, the run fluid mixes with the sample and the mixture is conveyed to the test membrane. In another preferred embodiment, the swab has a main tube and a capillary tube. A run detector in the capillary tube detects when an adequate sample of bodily fluid has been taken.

BRIEF DESCRIPTION OF THE DRAWINGS

Preferred embodiments of the invention will now be described in more detail, by way of example, with reference to the drawings in which:

FIG. 12 is a cut away side view of a third embodiment of a test swab;

FIG. 13 is a plan view of the test swab of FIG. 12;

FIG. 14 is a side view of the piercing spike for attachment to a test cartridge for use with the test swab of FIGS. 12 and 13;

FIG. 15 is a plan view of the spike of FIG. 14;

DETAILED DESCRIPTION OF THE PREFERRED EMBODIMENT

Figure 1:
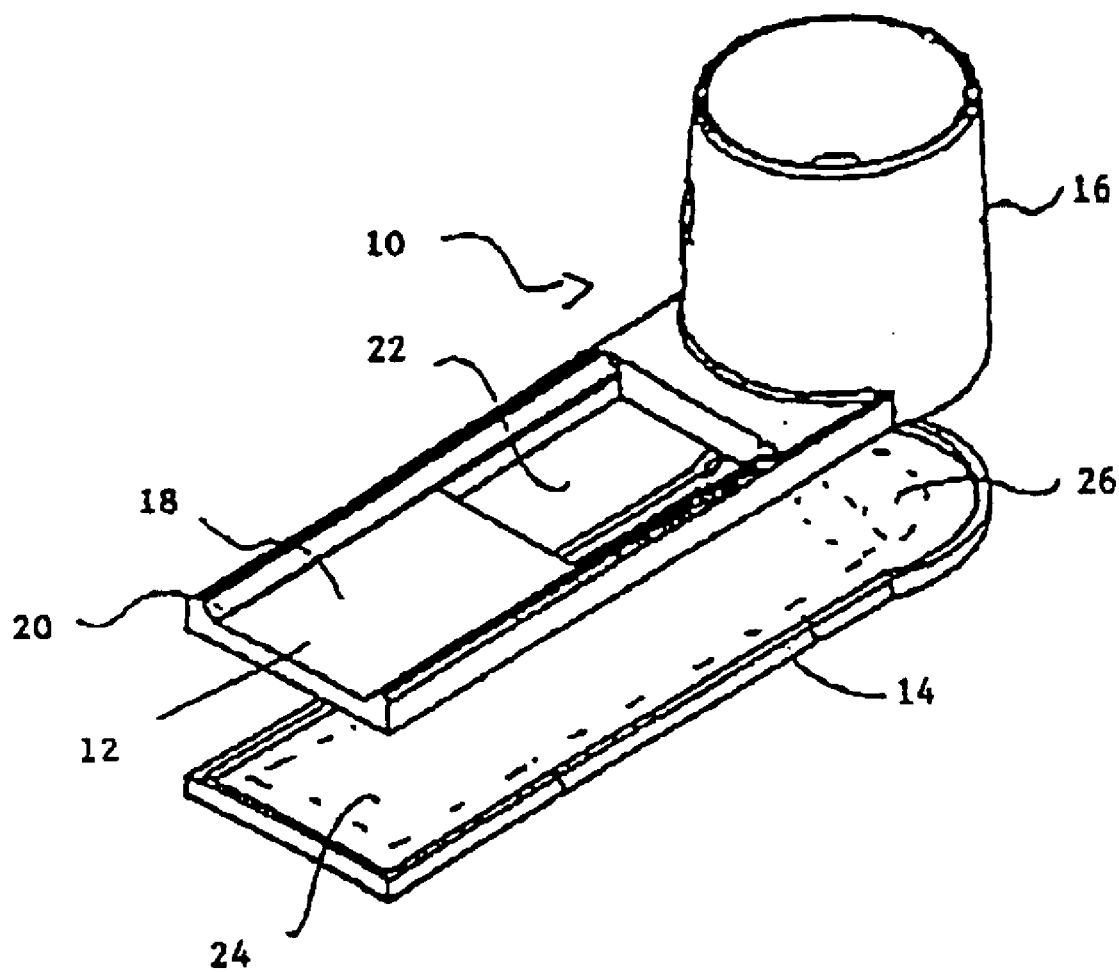
FIG. 1 is an isometric view of a test cartridge.

FIG. 1 shows a test cartridge 10 used to run the immunoassay tests to be screened by the screening device. The test cartridge 30 may be disposable and is formed from a top 12 and a base 14. The top 12 of the test cartridge 10 has a cylindrical swab holder 16 extending vertically from one of the shorter ends of an elongate tray 18. The swab holder 16 is open at both ends.

Ridges 20 extend upwardly from both of the longer sides of the elongate tray along the length of the tray. A rectangular window 22 extends transversely between the ridges 20 across the elongate tray and extends over a longitudinal length of the elongate tray which is less than the overall length of the elongate tray such that the window 22 is bounded on all four sides by the elongate tray 18. The window 22 extends through the entire thickness of the elongate tray 18.

Figure 2:
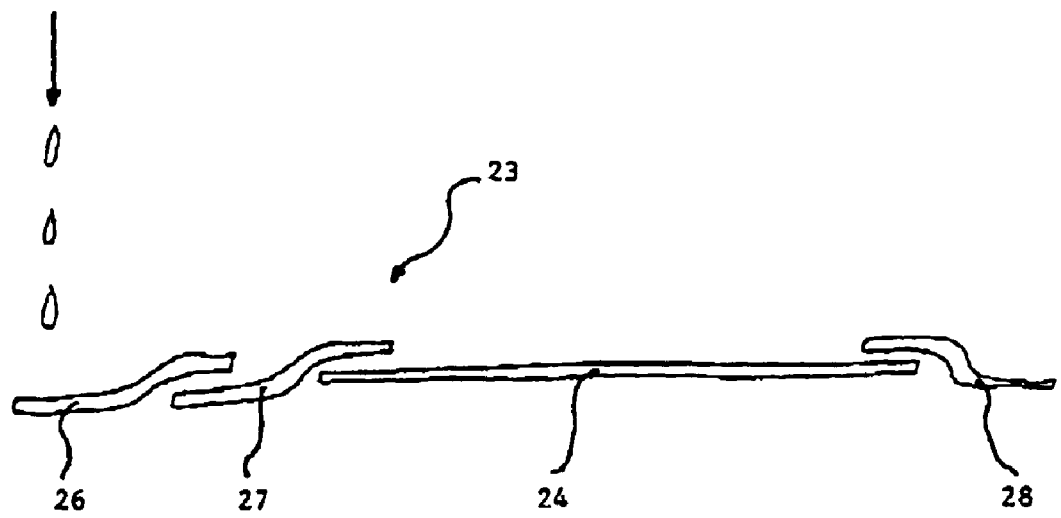
FIG. 2 is a side view of an immunoassay test strip.

FIG. 2 shows an immunoassay test strip 23. The upper surface of a flat, elongate nitrocellulose membrane 24 is bonded to a waste pad 28 at one end and to a conjugate release pad 27 at its other end. Both the conjugate release pad 27 and the waste pad 28 overlap the ends of the nitrocellulose membrane 24. The other end of the conjugate release pad 27 overlaps an absorbent sample pad 26 and is bonded at its upper surface to the lower surface of the absorbent sample pad 26. When fluid is applied to the sample pad 26 it is drawn along the sample pad by capillary action, through the conjugate release pad 27 and nitrocellulose membrane 24 and surplus fluid is absorbed by the waste pad 28.

The base 14 of the test cartridge 10 has a rectangular portion with a rounded portion at one end. An immunoassay test strip 23 is laid onto the upper surface of the base 14 with the sample pad 26 located in the rounded portion of the base 14. The immunoassay strip 23 (shown in dashed lines on FIG. 1) extends longitudinally along the length of the base 14 from the end of the base furthest from the rounded portion stopping within the rounded portion but short of the end of the rounded portion. The top 12 is then assembled onto the base 14 by fitting the cylindrical swab holder 16 onto the rounded portion of the base 14 and the elongate tray 18 of the top 12 onto the rectangular portion of the base 14. The top 12 and base 14 are joined for example by gluing. Alternatively, the top 12 may be designed to snap-fit onto the base 14. The top 12 may be made of a single unit so that the elongate tray 18 and the swab holder 16 are a single piece.

The conjugate release pad 21 holds a mobile and visible label, or marker, such as colloidal gold, and is in contact with the nitro-cellulose membrane 24 such that when fluid is added to the swab holder 16, it is drawn by capillary action downstream from the swab holder 16 through the absorbent sample pad 26 through the conjugate release pad 27 and subsequently through the nitro-cellulose membrane 24. The use of cartridges of this type is known in the prior art for example from EP 0291 194 by Unilever NV titled "Immunoassays and devices therefor".

At discrete intervals along the nitro-cellulose membrane 24 drug-protein derivatives are biochemically bound to the nitro-cellulose membrane, producing an immobile test zone of drug-protein derivative which spans the width of the nitro-cellulose membrane. Towards the extreme downstream end of the nitro-cellulose member, downstream of all the immobile drug-protein derivative test zones, is a control zone which also spans the width of the nitro-cellulose membrane. The test zones and control zone are interposed between background zones where the nitrocellulose membrane 24 does not have bound drug conjugate but has been blocked by other protein or other substances to prevent non-specific binding. Antibodies to each drug which is to be tested for, conjugated with colloidal gold, are placed on the conjugate release pad 27. When saliva is transferred from the swab in the presence of a run-fluid, the resulting sample passes across the absorbent sample pad 26 and across the conjugate release pad 27 where it mixes with the antibody-gold conjugates. The sample then travels the length of the nitro-cellulose membrane 24.

If the particular drug is present in the sample it will bind to the antibody-gold conjugate. When the bound drug subsequently passes over the specific drug-protein derivative test zone the antibody-gold conjugate has already been bound to the drug in the sample and is not free to bind with the drug-protein derivative bonded to the membrane. If the particular drug is absent from the sample, the antibody-gold conjugate will be free to bind to the drug-protein conjugate at the specific test zone causing the antibody-gold conjugate to become immobilised at the site of the drug-protein conjugate. The visible marker is deposited in the test zone as a coloured line or stripe. In between these two extremes some of the antibody-gold conjugate will bind with the drug-protein derivatives at the test zone on the strip creating an intermediate intensity of colour. The intensity of the colour on the particular drug-protein test zone is therefore inversely proportional to the amount of drug present in the sample.

The depth of colour of the control zone should always be significant and the control zone is designed with this in mind. The colour of the control zone can then be used to indicate that the assay test has been successfully run and to threshold colour levels in specific drug conjugate test zones.

Figure 3:
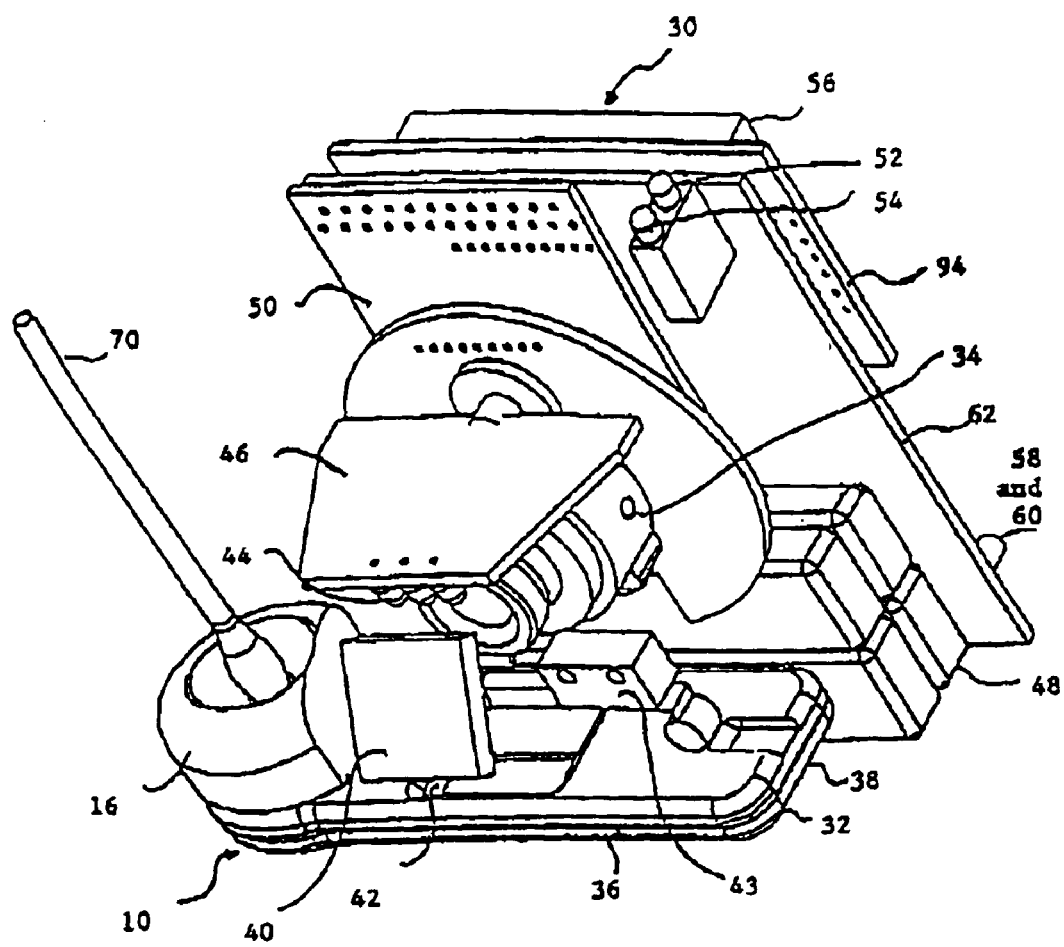
FIG. 3 is an isometric view of a preferred screening device embodying the invention with a test swab and test cartridge located ready for analysis.

FIG. 3 shows the test cartridge 10 of FIG. 1 located into the screening device 30. The screening device 30 includes a receiving section, an imaging section and a display section. The receiving section is located at the rear of the screening device and receives and aligns a test cartridge prior to the screening operation. The imaging section is located centrally in the screening device between the receiving section and the display section and includes the illuminating and imaging equipment, the processing capabilities and battery pack. At the front of the screening device is the display section for outputting the results of the screening operation. A cover (not shown) which is open at the front end of the screening device 30 encases the remaining five sides of the screening device 30. A facia cover (not shown) is attached to the cover to completely encase the screening device 30, protecting the screening device and the user from accidental damage.

The receiving section includes a receiving bracket 32 and a microswitch 43 and also positions and supports a half silvered mirror 40 which forms part of the imaging section. The receiving bracket 32 has a back 38 and two parallel arms 36. The back 38 is connected at either end to one end of each arm forming a U-shaped bracket. The open end of the U-shaped receiving bracket 32 is directed outwardly from the screening device 30 and is aligned with an opening in one side of the cover (not shown) towards the rear of the screening device 30. The opening is large enough to allow a test cartridge 10 to be inserted into the bracket 32 of the screening device 30. The arms 36 of the receiving bracket 32 are spaced apart by a distance equal to the width of the test cartridge 10 and have the same longitudinal length as that of the elongate tray 18 of the test cartridge 10. The arms 36 have a C-shaped cross-section. When a test cartridge is inserted into the opening the ridges 20 on the test cartridge 10 engage with the C-shaped cross-section of the arms 36 of the receiving bracket 32 to direct the test cartridge into the screening device 30. The test cartridge 10 is slidably inserted into the arms 36 of the bracket of the screening device 30 until the end of the test cartridge reaches the back 38 of the receiving bracket when pressure against further insertion will be felt.

A half silvered mirror 40, which forms part of the imaging section of the screening device, is supported above the window 22 of the test cartridge 10 by a column 42 extending upwardly from the outer arm 36 of the receiving bracket 32 nearest the rear of the screening device 30.

A test swab 70, holding a saliva sample, is located in the swab holder 16 of a disposable test cartridge 10. The test cartridge 10 is inserted into the screening device 30 by the end furthest from the swab holder 16 and is positively located in the correct screening position by receiving bracket 32. The back 38 of the receiving bracket 32 prevents the test cartridge 10 from being inserted too far into the screening device 30 and ensures that the window 22 of the cartridge 10 is located directly in front of and beneath the CCD 34 of the screening device 30. Electrical circuitry 50 controlling the operation of the screening device including operation of the CCD 34 are housed within the screening device 30 towards the front of the screening device 30 in front of the CCD 34, test cartridge 10, and rechargeable batteries 48.

A microswitch 43 is supported above the test cartridge 10 from the inner arm 36 of the receiving bracket 32 nearest the CCD 34. When a test cartridge 10 is fully inserted into the screening device 30 the microswitch 43 is displaced vertically causing an electrical signal to be emitted from the microswitch to signal that the correct insertion of a test cartridge 10 has been detected. During screening of the test cartridge 10, the microswitch 43 may resist any displacement of the test cartridge 10 once it has been fully inserted into the screening device.

The imaging section includes illuminating means, photosensitive detector means, means for representing the intensity of the detected light by a data array, data processing means for segmenting the data and comparing the segmented data and output means. The illuminating means is provided by three light emitting devices (LEDs) 44 which are mounted in a horizontal line parallel to the longitudinal length of the test cartridge 10 with the middle LED centred vertically above the centre of window 22 of the test cartridge 10. The photosensitive detector means and means for representing the intensity of the detected light by a data array are provided by the CCD 34 which includes an imager 82, a video digitiser 84 and a video data interface 86 (shown on FIG. 5). Alternatively, the photosensitive detector means may be made up from a CCD array device together with a control and data conversion interface. The imager of the CCD 34 is directed towards the rear of the screening device 30. A mounting plate 46 is attached to the upper body of the CCD 34 towards the front of the screening device 30. The mounting plate 46 extends horizontally from the body of the CCD 34 towards the rear of the screening device 30 and finishes directly above the window 22 of the test cartridge 10. Three LEDs 44 are attached in a row at the front of the underside of the mounting plate 46. When illuminated, the light from the LEDs 44 shines directly onto the window 22 of the test cartridge 10. The mirror 40 is inclined from the vertical by approximately 350 such that the window 22 of the test cartridge is reflected into the field of view of the CCD 34. Light reflected from the immunoassay test is detected by an array of photosensitive detectors in the imager 82. The photosensitive detectors emit an electrical signal proportional to the intensity, the concentration, of light detected. The video digitiser 84 scans each of the photosensitive detectors in turn, converting the analogue data to digital data and storing the data in an array. The array of digital data is subsequently outputted to a central processor unit (CPU) 80 via the video data interface 86.

Rechargeable batteries 48 supply power to the CCD 34, LEDs 44, microswitch 43 and electrical circuitry 50. The rechargeable batteries 48 are positioned towards the front of the imaging section below the CCD 34. The electrical circuitry 50 which forms the final part of the imaging section is described later with reference to FIG. 4 and FIG. 7.

At the front of the screening device 30 is the display section including two test indicator LEDs 52 and 54, a liquid crystal display device (LCD) 56, operating buttons 58 and 60 and a front plate 62. The front plate 62 is slightly smaller than the facia cover and is located at the front of the screening device 30 directly behind the facia cover. The two test indicator LEDs 52 and 54 are mounted at the top of the rear of the front plate with the LEDs 52 and 54 protruding above the level of the front plate 62. Holes in the top of the cover at its front corner allow the test indicator LEDs 52 and 54 to protrude through the cover such that they are visible on top of the device.

The LCD 56 and its associated backlight driver 94 are mounted at the top of the front plate 62 between the front plate 62 and the facia cover. The facia cover has a window through which the LCD 56 is visible but which obscures the backlight driver 94, located behind the LCD 56, from view. Also mounted onto the front plate 62 between the facia cover and the front plate are the two operating buttons 58 and 60. The facia cover has holes in corresponding locations to allow the user to operate the buttons 58 and 60 through the facia cover.

Additionally holes for an infra-red communication port and a serial and parallel link for connecting the screening device to a personal computer (PC) may be provided in the cover and corresponding connections from the electrical circuitry 50 may be provided.

Figure 4:
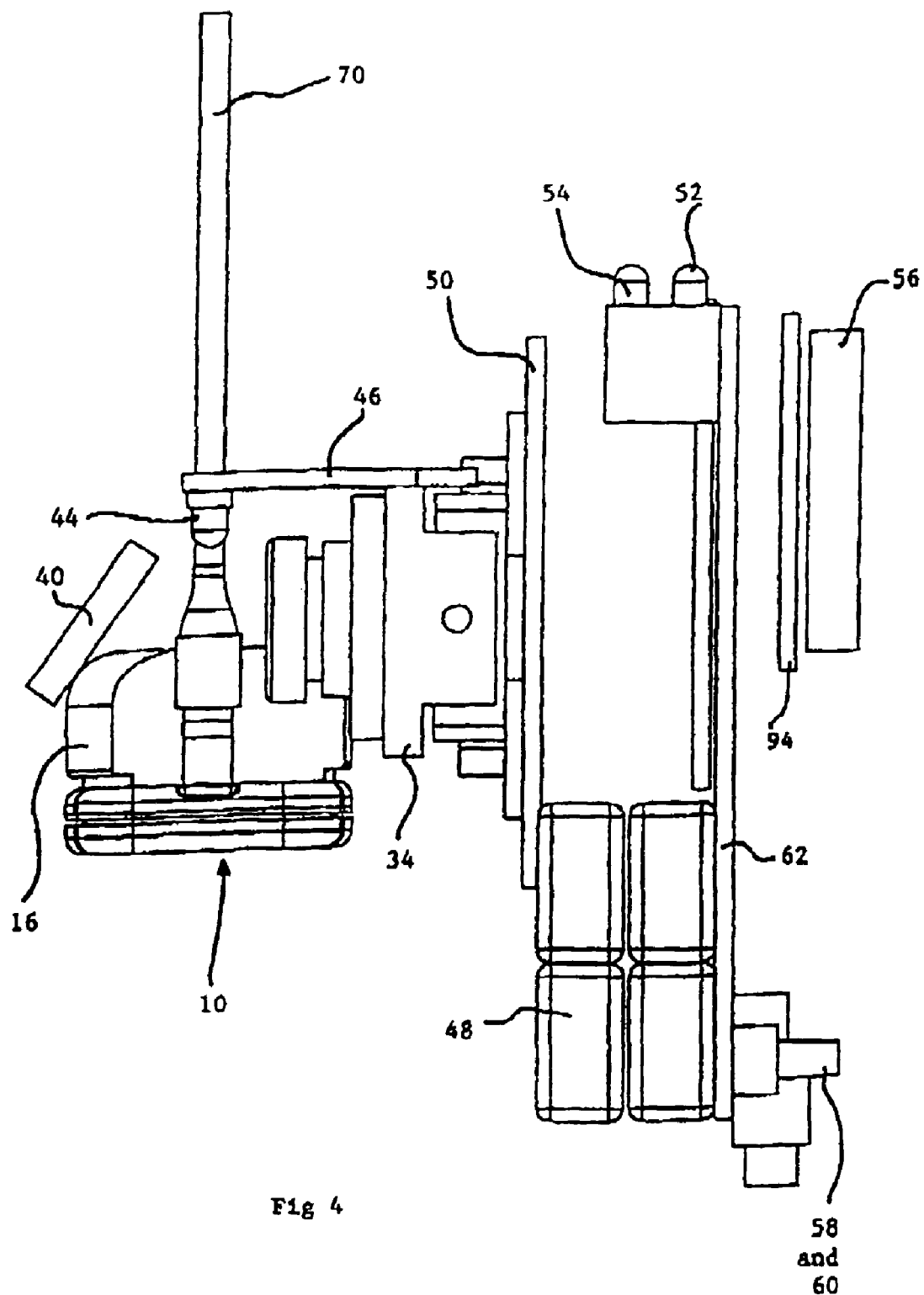
FIG. 4 is a side view of the screening device, test cartridge and test swab of FIG. 3.

FIG. 4 shows a partially sectioned side view of the screening device of FIG. 3.

Figure 5:
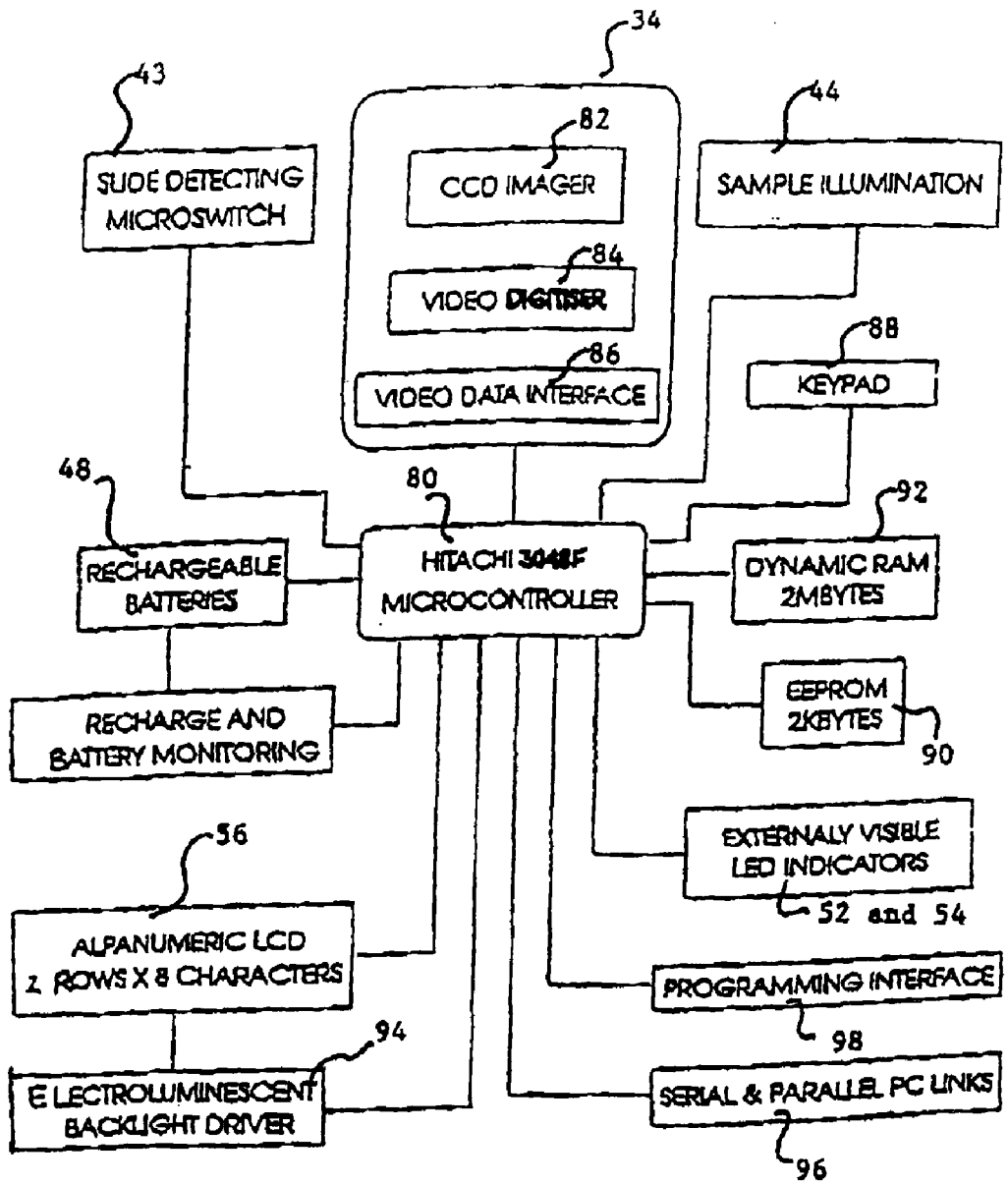
FIG. 5 is a block diagram of the electrical controls and electrical apparatus used in the screening device.

FIG. 5 shows a block diagram of the electrical components of the screening device 30. The screening device 30 is based around a microprocessor or central processor unit (CPU) 80 and the CCD 34. The CCD 34 comprises the imager 82, and associated video digitiser 84 and video data interface 86. The screening device may also includes a keypad 88 or may be operated via a combination of buttons provided on the facia. The screening device also includes electrically erasable read only memory (EEPROM) 90, dynamic random access memory (RAN) 92 and the liquid crystal display (LCD) 56. The EEPROM 90, RAN 92 and LCD 56 are connected to the CPU 80. Alternatively, the EEPROM and RAN may be internal to the CPU. The LCD 56 may be backlit and control is provided via a backlight driver 94 which is connected to both the CPU 80 and the LCD 56.

The keypad 88 may be used to allow a user to enter data required by the CPU 80 to control operation of the screening. device. Results from the screening device 30 are displayed to the user via the LCD 56 which also acts to prompt the user for the data required to operate the screening device. Power is supplied to the CPU 80, LEDs 44, LEDs 58 and 60, microswitch 43 and CCD 34 from the rechargeable battery pack 48. The batteries can be recharged from the main electrical supply or, for example from a car cigarette lighter, via an adaptor. The operation of recharging the batteries can be controlled by the CPU or alternatively can be controlled manually. Preferably, the screening device automatically shuts down to preserve battery life if no cartridge is present or if the results of the previous screening have been displayed for longer than a preset time, say 5 minutes. Preferably, if an external power supply is detected by the screening device the CPU 80 automatically commences a battery recharging program. Preferably, the batteries can hold enough charge to operate continuously for up to 24 hours without being recharged.

The CPU 80 controls an electroluminescent backlight driver 94 to backlight the LCD 56. Preferably, the LCD 56 is capable of displaying two rows each of 8 alphanumeric characters. In addition to the LCD display, two LEDs, one red 58 and one green 60, are provided. Illumination of the LEDs 58 and 60 is controlled by the CPU 80 and may be used to indicate visually the progress and status of the scant ie in progress, results ready for display, or the outcome of the test, Alternatively, the progress or results could be indicated by an audible signal. The LCD 56 may also display status information.

In the embodiment described above the overall size of the device is approximately 85 mm by 80 mm by 65 mm and the device weighs approximately 300 g. The test device is thus small, light weight, and portable. The CCD 34 may be, for example, a Connectix Quickcam, incorporating a CCD imager, video digitiser and video data interface.

Operation of the screening device will now be described. Disposable saliva test swabs 70 are stored in a sealed pack and one swab removed immediately prior to use. The swab should be removed from the pack by the person whose saliva is to be tested and is wiped under the tongue for approximately 15 seconds. The swab 70 is then inserted into the swab holder 16 of a disposable test cartridge 10. Ten drops of a run fluid, which may be of any conventional type, are added to the swab holder 16. The run fluid transports the sample of saliva from the test swab 70 to the absorbent pad 26 and onto the conjugate release pad 27, where the saliva and run fluid mixture mixes with the labelled (e.g. with gold, coloured latex particles carbon particles, fluorescents, or any other suitable label) anti-drug antibodies. The sample subsequently travels along the length of the nitro-cellulose membrane 24. At each test zone any unbound labelled drug antibodies are bound to the drug-protein derivative of the test zone. Any of the labelled antibodies which have not been bound to the test zones passes over the control zone where it becomes bound to the control zone. The result is a number of lines of varying intensity spanning the width of the membrane at points along the length of the nitro-cellulose membrane corresponding to the drug-protein derivative test zones and the control zone. Each drug-protein derivative test zone can be used to detect a different drug. The higher the concentration of the particular drug in the saliva sample, the less intense the colour in that drug-protein derivative test zone.

As soon as the test swab 70 has been located in the swab holder 16 the test cartridge 10 is inserted into the screening device by gently pushing the end of the cartridge furthest from the swab holder 16 into the opening of the screening device 30, allowing the test cartridge 10 to be guided by the receiving bracket 32. The test cartridge 10 should be inserted gently until the end of the test cartridge furthest from the swab holder 16 reaches the back 38 of the receiving bracket 32 when there will be resistance against further insertion.

Once inserted into the screening device the cartridge is left in position until the scanning process has been completed. A message on the LCD and/or flashing of the LEDs indicates that the scan is complete. Only then may the cartridge be removed.

As the test cartridge 10 is pushed into position it displaces the micro switch 43. A signal is sent from the microswitch 43 to the CPU 80 which activates the scanning process by down-loading a preset program from EEPROM 90. Timer means are provided to delay illumination of the immunoassay test strip until the test has had time to run. Once the presence of a test strip has been detected the CPU 80 commences initialisation by prompting the user to set a timer to alert the operator to wait a sufficient time for the sample to travel the length of the membrane. Alternatively the user may time the test manually and an on/off power switch can be provided which the user can operate once the assay test has been run and the test cartridge 10 has been inserted into the screening device 30. The timer function may be provided by a separate timer integrated circuit controlled by the CPU 80 or may alternatively be provided internally to the CPU 80. When the prerequisite length of time has elapsed, which is generally of the order of five minutes, the timer sends a signal to the CPU 80 which alerts the operator that the sample is ready for screening for example by flashing LEDs 58 and 60, displaying a message on LCD 56 or sounding an alarm. The screening device is also able to time the test, analyse results, output results and store the results automatically.

A plurality of adjacent membranes may be incorporated into a single test cartridge with the membranes running longitudinally the entire length of the cartridge from the absorbent pad to the end of the cartridge furthest from the swab holder and each membrane 24 having a transverse width less than that of the test cartridge 10 such that a plurality of membranes, for example two, may be placed side by side in the test cartridge 10. Processing the results of the saliva test depends on identifying the intensity of the lines on each membrane and relating each line to the drug which is the subject of that particular test. Details of the number of adjacent membranes in the particular cartridge and the number, type and position of the drug-protein derivative zones and control zone on each membrane are required for processing of the results. These details can be held in the EEPROM and accessed by the CPU 60 upon detection and recognition of the cartridge type or the user can directly enter data required for the CPU 80 to recognise the test cartridge 10. If the test cartridge 10 is to be recognised by the CPU 80 it may carry appropriate marking such as a bar code, which is read by appropriate means provided in the screening device and the information is passed to the CPU 80.

The test cartridge 10 may be printed with the name of the test which may be automatically read and identified by the CPU 80. The test cartridge 10 may also contain an implanted microelectronic circuit which may be interrogated by the CPU 80 by means of electrical, infra-red or inductive links in order to ascertain whether the cartridge is acceptable and to determine the nature of the test.

The CPU 80 enables the CCD 34 and switches on the appropriate LED 44, thus illuminating the window 22 of the test cartridge 10. In the presently preferred embodiment three LEDs are provided, with wavelengths of 430 nm, 565 nm and 660 nm respectively. The wavelength of light emitted by each LED is chosen with reference to the characteristics of the label, in particular to its colour. Preferably the wavelength of the light used to illuminate the immunoassay strip is complementary to the wavelength of the particular label in order to provide the best contrast. In the presently preferred embodiment, colloidal gold is employed as the label and as colloidal gold is pink in colour a green LED with a wavelength of 565 nm is used. Whilst the label has been described as visible and the example of colloidal gold as a label would be visible to the human eye, the label may be chosen to be visible to the CCD array under certain lighting conditions and may not, either under normal lighting conditions or under special lighting conditions, be visible to the human eye.

Light from the LED 44 shines onto the window 22 of the test cartridge 10 illuminating the nitro-cellulose membrane 24 visible through the window 22. The illuminated membrane 24 is reflected by the mirror 40 into the field of view of CCD 34. The image is digitised and outputted via a video data interface to the CPU 80 for data processing. Preferably, the digital data is stored to dynamic RAM 92 for subsequent processing.

The image captured by the CCD 34 is skewed by the reflection from the mirror 40 and the CPU 80 must first apply an algorithm to correctly align the digitised data for processing. Preferably, the CPU 80 runs an initial correction algorithm to arrange the data for subsequent processing. Preferably the initial correction algorithm is set when the device is manufactured and, if necessary, calibrated, at points during the life of the device rather than at the beginning of each test.

Each cartridge may be used to run tests for a number of different drugs. This can be achieved either by using a single membrane with a larger number of drug-protein derivative zones or using a number of membranes in a single cartridge. Up to eight or more drugs may be analysed at any one time using a combination of these methods. In the presently preferred embodiment, drug-protein derivatives for cannabis (THC), cocaine (COC), opiates (OPI), methadone, ecstasy and amphetamines (XTC) and benzodiazepines (BZO) are bound to the nitro-cellulose membrane at discrete intervals. The results for each of these drugs tests is indicated separately by the screening device. Two panel tests, for example for methadone and opiates, may also be provided. The data must then be segmented such that each segment relates to one membrane only. The separate segments are then processed separately. In the presently preferred embodiment the CCD array is a Texas TC 255 P CCD array which is made up of 324×240 elements. The digital data must be segmented to correspond to the 344×240/N pixels covering that particular membrane only where N is the number of membranes in the cartridge.

Each membrane is therefore represented by an array of p×q pixels where the p pixels span the length of the membrane and the q pixels span the width of the membrane. The drug-protein derivatives are bonded across the entire width of the membrane at discrete intervals along the membrane. At any location (p,r) where p falls within a particular drug-protein derivative test zone the intensity of the pixel is related to the amount of that particular drug in the sample, regardless of the value of r in the range $0 \leq r \leq q$. The intensities of the pixels at (p,r) are therefore summed over the range $0 \leq r \leq q$ for each p.

Slight discrepancies between the theoretical position of the membrane and the actual position of the membrane may be accommodated by the screening device. The CPU 80 compares the summed intensity at a specific location corresponding to the theoretical centre position of the control zone with the intensity at a predetermined number of adjacent locations to determine whether there is any discrepancy between the theoretical location of the control zone with the actual location of the control zone. The CPU 80 applies a corresponding offset to subsequent calculations if the theoretical and actual locations of the centre of the control zone differ. The offset must be determined by reference to the control zone because if any of the tests are positive then the intensity of that drug-derivative test zone will be correspondingly reduced.

Alternatively, or in addition, the test strip 23 and test cartridge 10 may be of contrasting colours. The unskewed data may be processed using the contrast between the test cartridge 10 and the test strip 23 to determine the actual location of the centre of the test strip which may then be used to apply an offset to the data if required.

Figure 6:
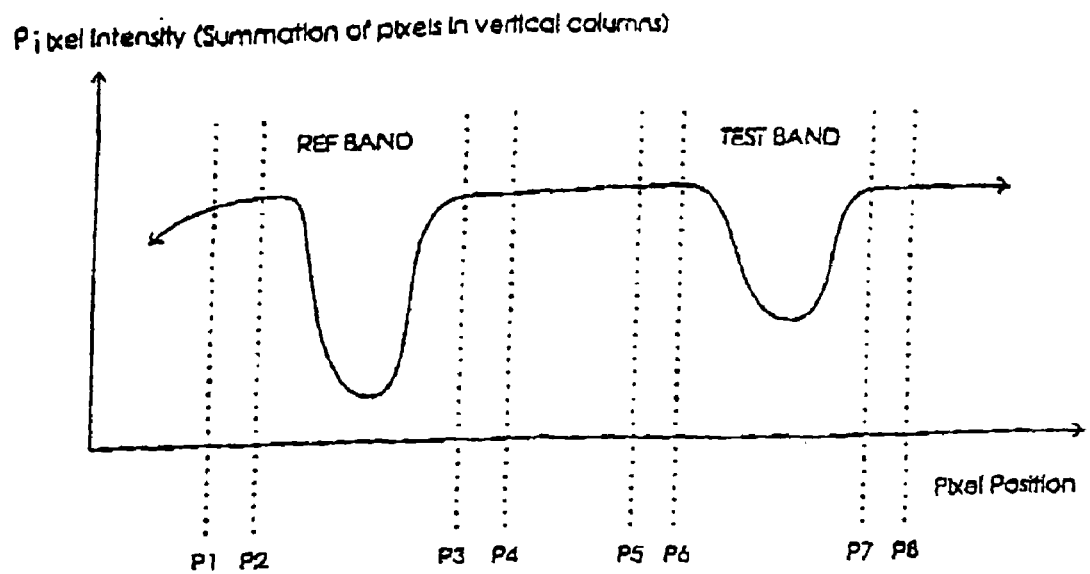
FIG. 6 shows a graph of the typical variation of pixel intensity with pixel position for a single test and a single reference test.

FIG. 6 shows a typical graph of the resulting pixel intensity against the location of the pixel for a single protein-drug derivative test zone and a single control, or reference, zone. Once any offset of the membrane from the theoretical position has been identified, the data is segmented according to whether it lies in a drug-protein derivative test zone, the control zone or in a space (i.e. a background zone) between adjacent zones as shown in FIG. 6. Preferably, the CPU 80 is a Hitachi H8/3002 microprocessor chip but any other suitable microprocessor chip may be used. The CPU 80 segments the data into a first plurality of data corresponding to the control zone, a second plurality of data corresponding to the test zones, and a third plurality of data corresponding to the background zones. The CPU 80 then processes the first, second and third pluralities of data, performing the following calculations to determine whether each drug is present in the sample.

$$RW1 = \sum_{p1}^{p2} \qquad RB = \sum_{p2}^{p3} \qquad RW2 = \sum_{p3}^{p4}$$

and $$TW1 = \sum_{p5}^{p6} \qquad TB = \sum_{p6}^{p7} \qquad TW2 = \sum_{p7}^{p8}$$

Then estimate $$REF = 1 - \left( \frac{2RB}{(P3 - P2 + 1)(RW1 + RW2)} \right)$$

and $$TEST = 1 - \left( \frac{2TB}{(P7 - P6 + 1)(TW1 + TW2)} \right)$$

If $REF \leq 0$ then the reference, or control, zone has not bound any of the products present in the saliva sample and run fluid after it passed over the drug-protein derivative test zones. Either the control zone is faulty on the membrane or the assay test has not been completed correctly which may be due to an insufficient amount of run-fluid being added to the swab holder. The screening device will display an error message and the cartridge should be removed, reinserted and reread or disposed of and another cartridge run. However, the delay for the test to be performed is not required in these circumstances and the operator is provided with a means for bypassing the timer operation to commence immediate image acquisition and data processing. If an error is still detected then the test must be re-run using a new cartridge and saliva sample.

If REF>0 showing that the assay test has been successfully completed but TEST≦0 then the drug concentration in the sample is such that all the antibody-gold conjugates have been bound to the drug in the sample. The results of that test is set to 100%. The test is assigned a qualitative level "Positive". A quantitative value would be represented as "greater than" a certain level.

If TEST>0 and REF>0 then the test band concentration is determined as follows:

$$\text{TEST BAND CONCENTRATION} = 1 - \left(\frac{TEST}{REF}\right)$$

The percentage of drug present in the sample is given by 100×Test Band concentration %.

The results for the concentration of each drug can be displayed in a number of ways. The LCD 56 may be used to display the name of the drug and its result. Alternatively only the fact that the test for that particular drug is positive may be displayed. If the display is to indicate a positive or negative result only then the CPU 80 must have access to a threshold for each drug which could be held in the EEPROM. For each drug if the detected concentration exceeds the threshold then the result would be positive and if the detected concentration falls below the threshold then the result would be negative. Each separate drug-protein test zone must be tested in this way with reference to the control zone to determine the concentration of that drug in the saliva sample.

Alternatively, or in addition, positive and negative results could be displayed using combinations of the LEDs 52 and 54 provided on the top of the screening device. In the presently preferred embodiment, the red LED 52 will be continuously illuminated and the green LED 54 intermittently illuminated to indicate that the particular drug test is positive, and the green LED 54 will be continuously illuminated with the red LED 52 flashing if the drugs test is entirely negative. The operator may step through the result of each individual drug test by operating the buttons 58 and 60 on the front of the screening device or may view all the results simultaneously by down loading the results to a pc with the necessary graphics facilities. Results may be stored within the screening device until they are down-loaded to a PC. The test image may be stored for subsequent downloading to a PC.

If the test indicates that any of the drugs are present in the sample, follow up testing using an alternative test method may be performed.

The CPU 80 is provided with a programming interface 98 to allow the screening device to be programmed for example from a remote PC. Serial and parallel PC links 96 and/or an infra-red link may provided from the CPU 80 allowing the control of the screening device to be relinquished to a pc or mainframe computer. Results of the testing can also be displayed by the pc having been down loaded from the screening device. Preferably, the CPU 80 is capable of running self-testing diagnostic routines stored in EEPROM at intervals which may be controlled either by presets in the CPU or may be initiated on demand by the user.

In certain situations it may be preferable for the screening device operator to be provided with a display indicating the image produced by the CCD 34. An interface for the CCD 34 may be provided to allow the operator to view the image on a small graphics panel.

It may also be preferable to provide means for storing the image of the person who provided the test sample. For this purpose, the mirror 40 could be adjusted between the test screening position and a second position which allowed the image of the person being tested to be reflected onto the imaging means for storage and subsequent retrieval. Additional optical apparatus, for example a lens, may be required to modify the focal length along the external light path.

Figure 7:
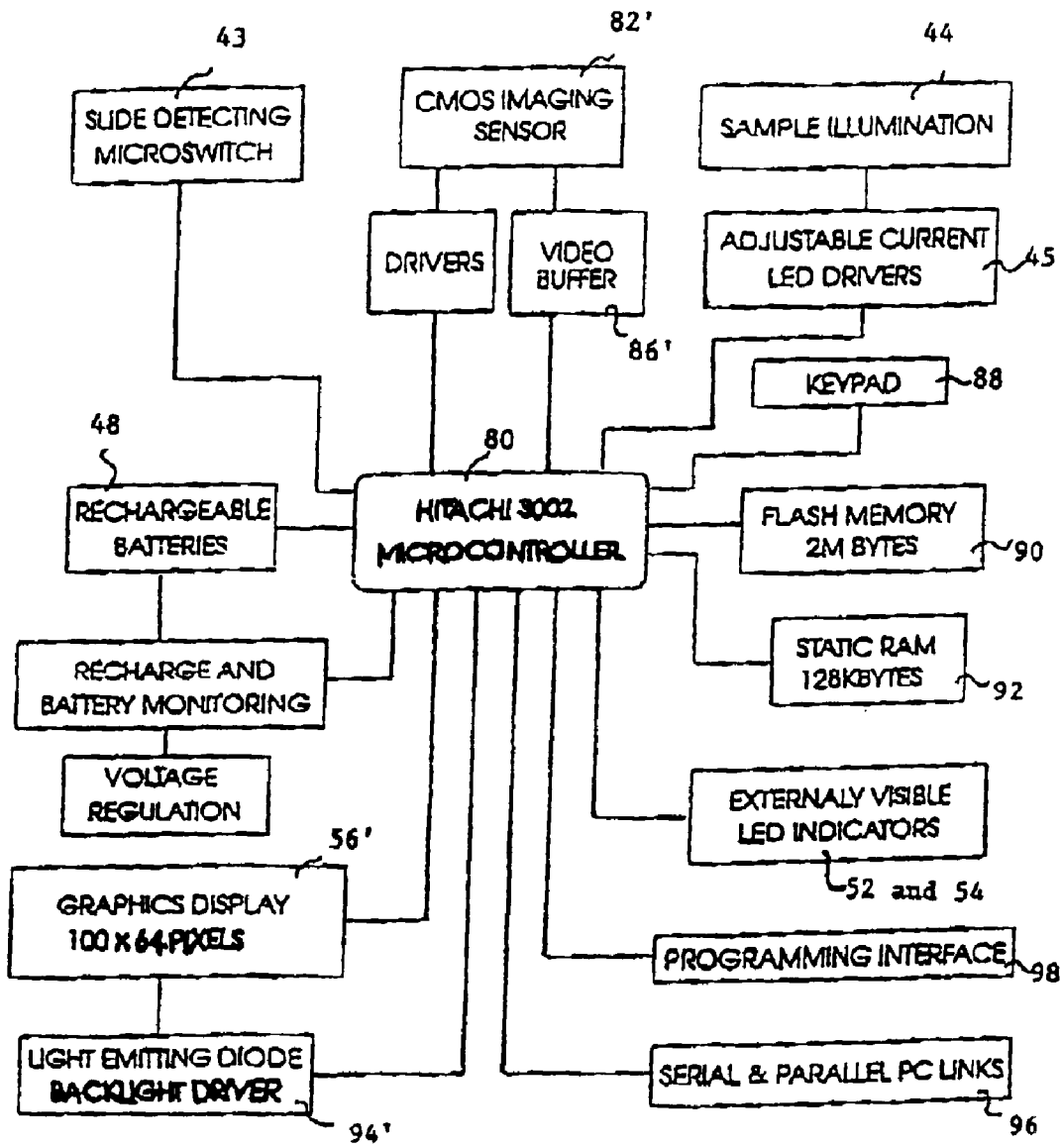
FIG. 7 is a block diagram of the electrical controls and electrical apparatus which may alternatively or additionally be used in the screening device.

FIG. 7 shows a block diagram of the electrical controls and electrical apparatus which may also be used in the screening device. Apparatus and controls which correspond to those of FIG. 4 are given the same reference numerals and reference should be made to the description above.

In particular, a CMOS image sensor 82' may be used instead of a CCD image sensor. A driver is associated with the CMOS image sensor 82' and interfaces between the CPU 80 and CMOS image sensor 34'. A video buffer 86' replaces the video data interface 86 of FIG. 5. Preferably, a Vision VV5404 imaging device having a resolution of 356×292 pixels is used.

The electroluminescent backlight driver 94 shown in FIG. 5 may also be replaced by light emitting diode backlight driver 94'. Furthermore, the volatile memory device 90 provided by an EEPROM in the apparatus of FIG. 5 may be replaced by FLASH memory and/or the non-volatile memory provided by the dynamic RAM (DRAM) in FIG. 5 may be replaced by static RAM (SRAM). An LCD 56' with a higher resolution capable of handling graphics of 100×64 pixels may also replace the LCD 56 of FIG. 5. This would allow all the test results to be displayed simultaneously if required. Batteries which are capable of holding sufficient charge to power the screening device for up to 20 days may be provided.

Preferably, means 45 for adjusting the intensity of each of the LEDs 44 nay be provided. Adjustable current LED drivers may be used as shown in FIG. 7.

The half silvered mirror 40 of FIGS. 3 and 4 may be replaced by a plain first surface mirror 40. The angle of the mirror and the imaging device may be altered to reduce the skew of the image. For example, by adjusting the angle of the mirror 40 to 55° to the vertical and using a CMOS image sensor inclined at 10° to the vertical, the combined inclination of the CMOS image sensor 82' and the mirror 40 minimises the difference in the image width over the width of the test strip with the result that the image captured by the CMOS image sensor 82' is substantially unskewed relative to the actual immunoassay test strip 23. In the case that the image captured by the imaging device is unskewed, the CPU 80 is not required to apply an algorithm to correct the digitized data prior to processing the data.

Different numbers of LEDs 44 may be used to illuminate the test strip 23. For example, four LEDs rather than three may be mounted in a horizontal row parallel to the longitudinal length of the test cartridge. If four LEDs are used, the two outermost LEDs may be chosen to emit light of one wavelength whilst the two innermost LEDs may be chosen to emit light of a different wavelength, With this configuration, only one pair of LEDs may be used to illuminate the immunoassay test strip 23 for the purpose of determining the drug concentration. The remaining pair of LEDs may be used for non-disruptive messaging, for example reading a bar code on the test strip or cartridge. The intensities of the LED pairs may be matched to provide optimal illumination of the immunoassay test strip 23. Suitable wavelengths for the LED pairs are 566 nm and 639 nm. However, the primary requirement in choosing suitable LEDs is that the wavelength of light emitted is compatible with the marker used on the immunoassay test strip 23 and that illumination of any messaging markings does not corrupt the test results.

The size and weight of the screening device may be affected by the choice of electrical apparatus and controls. Using a Vision VV5404, the overall dimensions and weight of the screening device may be 210×70×50 mm and approximately 240 g.

The control band may only be used to verify that the test has run successfully and may not be used for the quantification of individual drug concentration calculations. In this case, null data, reference data, may be provided in order to quantify the test results. Such null data may, for example, correspond to the data which would be generated by illuminating a blank immunoassay test strip under identical conditions to the illumination of the experimental immunoassay test strip. Such null data would then give an estimate of the intensity observed when the concentration of a drug in the sample under test approximates or exceeds the amount of conjugated antibodies released from the relevant pad. Such null data may be compared to the test data to determine the concentration of the substance in the sample under test.

Null data may be approximated by suitable filtering of the experimental data eliminating any need for separate illumination of an unused, clean test strip as a reference strip, For example, data corresponding to the length and width of one of the background zones may be interpolated to produce an estimate of the intensity that is representative of null data. Prior to interpolation, the data may be smoothed to improve the null data. More sophisticated filtering techniques, including adaptive filtering, may also be used in estimating the null data. Once null data has been estimated or provided, the test data and null data may therefore be compared to determine the concentration of the substances in the test zones.

Figure 8:
FIG. 8 is a schematic view of the detected intensity of a test strip showing the typical appearance of a control and test zone after a test has been run.

FIG. 8 shows schematically typical results of the appearance of a control zone and test zone thus detected by a CCD or CMOS image sensor on a test run on a sample of body fluid. The depth of colour of the control and test zones vary over the width and length of the zones resulting in an uneven appearance. However, in general the depth of colour towards the centre of the zones is deeper than at the outer edges, When the test strip is illuminated by an LED of complimentary wavelengths to the label used, the irregularities of the test and reference zones result in higher optical absorbency at the centre of the zones. Additionally, if the illumination over the length and width of the strip is not uniform, the CCD or CMOS image sensor will detect variations in the reflected lights intensity which are entirely independent from the test results.

In order to reduce illumination irregularities and hence suppress spurious test results, multiple error LEDs may be used to illuminate the test strip. Preferably each LED has an individually adjustable current. CPU 80 may be used to control the current supply to each LED to reduce such illumination irregularities and hence improve test results.

A further cause of the irregular appearance of the zones as detected by the CCD or CMOS image sensor is the variation in path lengths travelled by photons reflected from different parts of the surface of the immunoassay strip. This effect cannot be eliminated by a fixed pattern correction algorithm because to be most effective such correction should take account of any slight change of location of the test strip in relation to the mirror and/or CCD or CMOS sensor. Differences, however small, between screening devices mean that it is not possible to define a single fixed pattern correction algorithm for all devices.

In order to minimise the effects of these variations the CPU 80 may digitally filter the data once the alignment algorithm has been applied. Data corresponding to the entire test strip including the control zone, test zones and background zones is filtered. Each membrane is represented by an array of P×Q pixels where P pixels span the length of the membrane (rows) and Q pixels span the width of the membrane (columns). Across the width of the membrane the intensity of pixels in each column would, under ideal conditions, be identical. In practice, due to one or more of the irregularities described, the intensity of the pixels in each column vary to a greater or lesser degree. Thus the intensity of the pixels in each column are summed and the mean value stored in a 1–d column intensity data array.

Next, the centre of each of the test, control and background zones is estimated. The amount of marker deposited during the test tends to be greater at the centre of the test and control zones than at the edges of the zones. Hence, when the strip is illuminated by an LED of a complimentary wavelength to the marker, the intensity of the pixels reaches a local minimum close to or at the centre of each of the test and control zones. The geometry of the test strip being known, it is a simple matter to determine the number of pixels spanned by any one zone. In practice, the test and control zones preferably span 40 pixels. However, zones of widths corresponding to any number of pixels reasonable to achieve the desired resolution may be used.

The total intensity for each test and control zone is estimated by summing the data in the 1–d column intensity data array over that zone having used the local minimum intensity to locate the centre of that zone and knowledge of the width of the zone to determine how many data entries centred around the local minimum entry correspond to that particular zone.

Although the method described so far takes into account any irregularities in the deposit of the marker over the width and length of the strip, it does not take into account any illumination or uniformity. This may be achieved using information from the irregularities detected in the background zones where no marker should be deposited.

The data of the 1–d column intensity data array may be corrupted by noise and noise reduction is therefore performed. The filter achieves noise reduction by minimising excessive differences between entries whilst retaining the underlying signal (intensity of contrast between test zones and background zones). Any MA filter producing a symmetrical response (ie one where no spatial displacement or phase-shift is present in the output) may be used. In the presently preferred embodiment, a moving average filter of window length 3 columns is applied to the array. Longer window length filters may produce better smoothing of the data and hence improved noise reduction. The length of the filter window is limited by the spatial distribution of the coloured particles deposited. The window size of the filter must be chosen to be much smaller than the spatial distribution of the coloured particles deposited. Although longer window length filters produce better smoothing, they require a large amount of memory for processing and implementation is algorithmically less efficient than shorter window length filters. However, the smoothing effect achieved by a longer window length filter may be approximated by applying a smaller window length filter multiple times to the data. The 1-d data array is therefore copied and filtered three times using a moving average filter of window size 3 columns. The output of the filtering operation is retained in memory for use later as the non-interpolated image data.

A second moving average (MA) filter is used to interpolate the data to estimate a white, background level (ie to approximate the data that would have been obtained had the test bands not been present). The second filter must have a window length sufficient to span the width of the control and test zones. It is applied to the noise reduced data array which is outputted from the first MA filter. Preferably, when the width of the test and control zones is 40 columns, the width of the second MA filter is 41 columns. Preferably, the second MA filter is repeatedly applied to the array. In one embodiment of the present invention, the second MA filter is applied 21 times to the array. In particular, applying the second filter a number of times to the data improves the interpolation accuracy of the data corresponding to the test zones. Applying the filter 21 times has been found to be particularly effective for test zones which span approximately 13 elements of the data array. The choice of window length is a compromise between a requirement for excessive processing and achieving a reasonable estimate of the white background level. The filter should preferably be applied a number of times equal to or larger than approximately 1.5 times the width of the test zones in the data array entries. On each pass of the second MA filter each value of the data array is only updated by the filter output if the filter output is greater than the current value of that value of the array. If the output of the filter is smaller than the current value of the array, the current value is retained. This process allows the effect of the absorbency across the test on control zones to be minimised and a cleaner "white" background signal to be estimated. Typically, when the white background level is estimated from the 1-d data array (rather than on the original 2-d data array) the performance of the above described process is superior to alternative methods using interpolation of the background by applying a polynomial curve fitting approach. The output of the second filter is supplied to a third moving average filter.

The third MA filter is applied to the output of the second MA filter to remove any spurious peak values or spikes in the data. The third MA filter of width 11 columns is preferably applied twice to the array. Preferably, the window length of the third MA filter is chosen to be approximately equal to the width of the test zones in pixels. When the width of the test zones is approximately 13 pixels as in one presently preferred embodiment, a choice of 11 for the window length of the third MA filter is presently preferred. The processed, white background array is then used with the total intensity data generated for each test and control zone to estimate the ratio of intensity in each test zone for the background zones and the intensity of the control zone to the background zone. The resulting ratio for the control zone is then compared against a pre-set threshold to confirm that an appropriate amount of the marker has been deposited in the control zone to indicate that the sample has run successfully and that the amount of marker deposited in the control zone corresponds within limits to the amount expected. If the results of the comparison are negative, a fault condition is reported to the user, the results are ignored and a repeat test is required.

It will be readily apparent to a person skilled in the art that the filtering operation could be performed differently to achieve the same effect. For example, the white background signal may be estimated from the 2-d data array by using linear estimation of several pixel pairs located at offsets approximately half the inter-test zone spacing from the central pixel whose background value is being interpolated. Typically, these pairs lie in the white background zones between test zones and their mean value gives a good estimate for the background intensity in test zone locations. Interpolation of the 2-d data array may be carried out and column totals taken subsequently to form the 1-d data array. An advantage of this technique is that the location of the window of the cartridge (and therefore of the relevant portion of the test) may be performed more reliably. The test zones are virtually eliminated from the 2-d array without introducing other distortions allowing the periphery of the window of the cartridge to be located more easily. This method may be particularly effective at accurately interpolating the background when the test zones are very faint. Faint test zone colour concentration frequently arises for drug tests where the concentration of drug present in the sample is close to the threshold value which determines whether the test is positive or negative.

Figure 9:
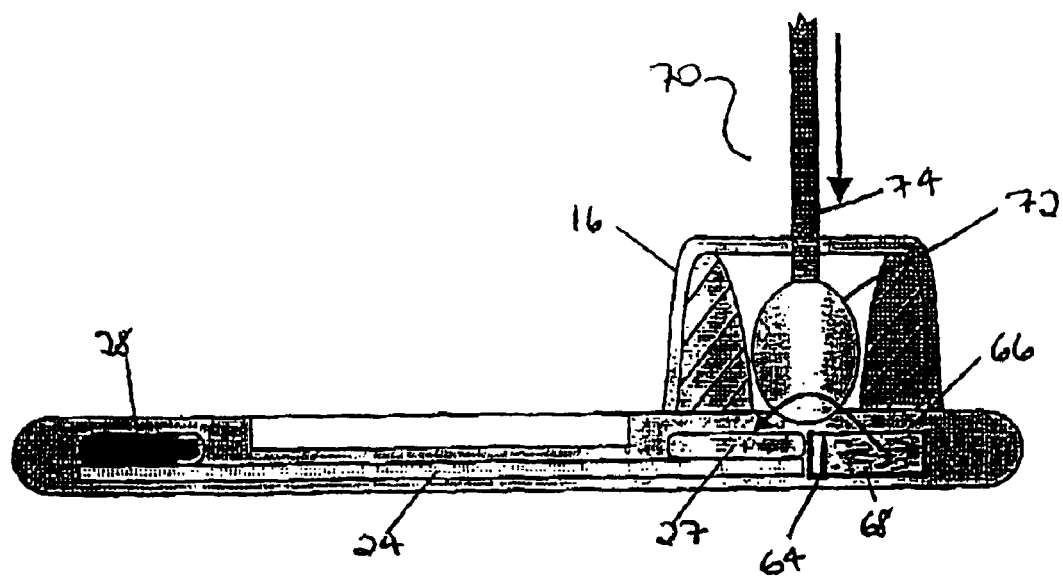
FIG. 9 is a cut away side view of a second embodiment of a test cartridge.

For use in adverse weather conditions, various adaptations (not shown in FIG. 1) to the test cartridge may be provided. A retractable, transparent cover may be provided on the test cartridge to protect the immunoassay test strip 23 which is otherwise exposed through the window 22, for example from exposure to rain. The window is retracted automatically upon insertion of the test cartridge into the screening device and is redeployed when the test cartridge is removed from the screening device. As shown in FIG. 9, the run fluid may be contained in a trough 68 within the cylindrical swab holder 16 or the test cartridge 10. The run fluid is held in place by a thin penetrable membrane 66 that covers the trough 68 until the test cartridge is used. The membrane 66 is pierced by spike 64 when the membrane 66 is deformed downwardly by the introduction of a test swab 70 into the swab holder 16. The run fluid is drawn by capillary action across to the conjugate release pad 27 via the saliva collection pad 72 of the test swab 70. If the operator exerts too much force on inserting the test swab 70 into the swab holder 16, the membrane 66 may rupture in an explosive manner causing the run fluid to be splashed onto the conjugate release pad 27 without first passing over the saliva collection pad 72. If the operator does not use enough force on inserting the test swab 70 into the swab holder 16, the membrane may not be pierced by the spike 64 and the test will not run. These problems are minimised and operator error reduced or eliminated by providing an internal thread on the bore of the swab holder 16 and the handle 74 of the test swab 70 may be provided with an external thread. The saliva collection pad 72 is placed into the swab holder 16 and the handle 74 of the test swab 70 is screwed into the swabholder 16 until it reaches an end stop. This allows controlled piercing of the membrane 66 on trough 64 and hence the controlled release of the run fluid to the saliva collection pad 72.

A second, elastic membrane with an aperture may be positioned above the run fluid membrane in the cylindrical swab holder 16. The aperture of the elastic membrane expands to allow a test swab to be inserted through the aperture and would form a waterproof seal around the test swab 70 prior to the test swab piercing the run fluid membrane. Upon removal of the test swab 70, the aperture of the elastic membrane contracts preventing fluid, other than that on the test swab, from entering the test cartridge.

Figure 10:
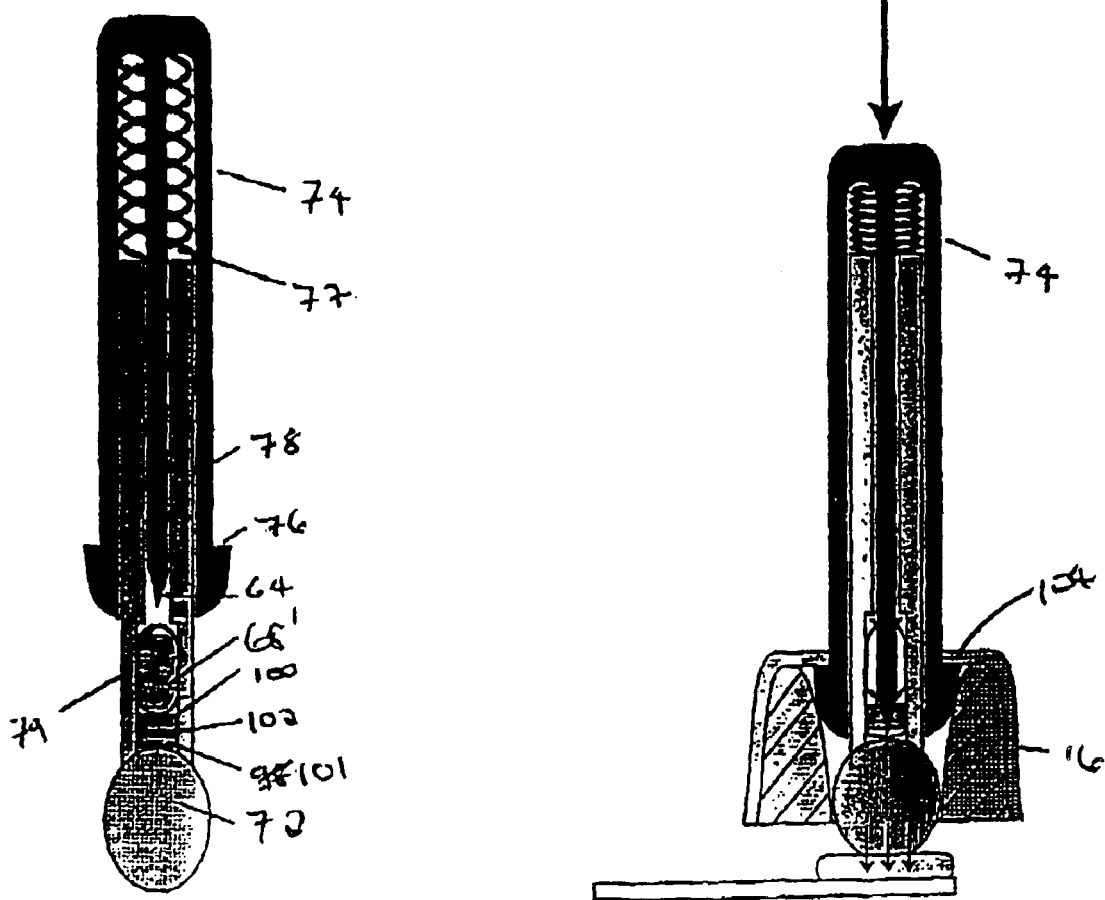
FIG. 10 is a cut away side view of a second embodiment of a test swab.

FIG. 10 shows a cut away side view of a second embodiment of a test swab which incorporates both the spike 64 and the run fluid within the test swab, and thus removes the need for these to be provided in the test cartridge.

The handle 74 of test swab 70 is made from a transparent is outer tube 78 open at the lower end thereof and closed at the top end thereof. At the lower end of the outer tube 78 a flange 76 is provided which protrudes outwardly from the outer tube 78. The flange 76 may extend around the entire periphery of outer tube 78 or may extend only around part or parts of the periphery of outer tube 78. An adequate spike 64 extends from the closed top end of the outer tube 78 downwardly. Alternatively, instead of a spike, a pin or any other sharp protrusion may be used.

A saliva collection pad 72 is attached to the lower end of tube 79. The tube 79 is open at both ends. The diameter of the bore of the tube 79 is large enough to allow the spike 64 attached to the outer tube 78 to enter the bore. Adjacent to the saliva collection pad 72 inside the bore of tube 79 are positioned in order a filler pad 101, dye release pad 102, a dye receptor pad 100 and a run fluid capsule 68'. In the embodiment shown in FIG. 10, the run fluid chamber 68' is a capsule. The run fluid capsule 68' is positioned closest to the upper end of the inner tube 78. The tube 79 has a diameter slightly less than the internal diameter of the outer tube 78 such that the tube 79 may be positioned within the outer tube 78 and moved vertically relative to the outer tube 78. To assemble the swab, a spring 77 is placed in the outer tube 78 through the open lower end and the tube 79, which effectively forms an inner tube, is inserted into the outer tube 78 to hold captive the spring 77. In the assembled position, the saliva pad 72 and lower part of the tube 79 encasing the filter pad 101, dye release pad 102, dye receptor pad 100 and run fluid capsule 68' protrude below the lower end of the outer tube 78. The spike 64 is held remote from the capsule 68'. In this sampling position, the swab may be used to collect a sample of bodily fluids. The length of the spike is determined by the maximum displacement of the tube 79 relative to the outer tube 78 such that the spike 64 may be used to puncture the run fluid capsule 68' when the tube 79 is forced, against the pressure of the spring 77, into the outer tube 78. The tube 79 is transparent and the outer tube 78 may also be transparent.

Figure 11:
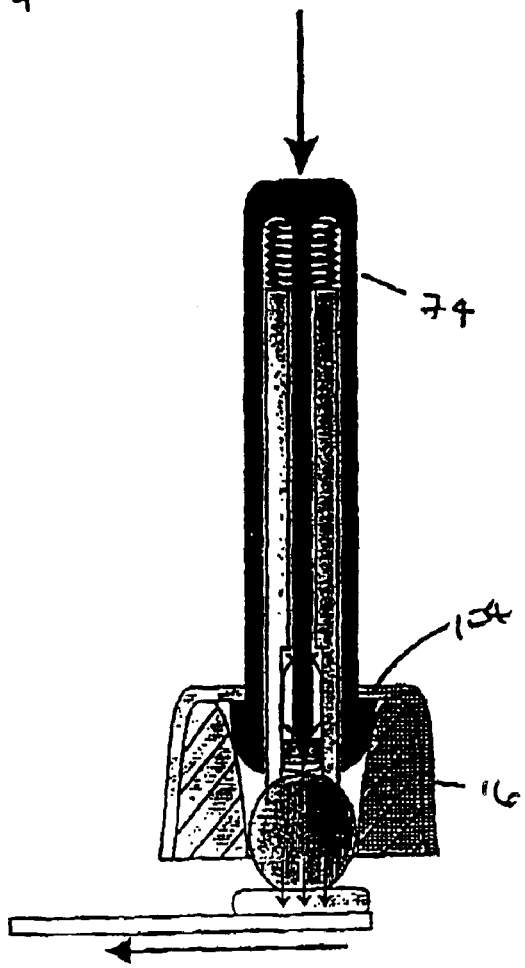
FIG. 11 shows the cut away test swab of FIG. 10 inserted into a test cartridge and deployed for running a test.

With the elongate spike held in the sampling position (i.e. disbursed from the capsule 68'), a saliva collection pad 72 of the test swab 70 is inserted into the mouth of the person to be tested and saliva collected until the saliva migrates by wicking effect up the saliva collection pad 72 through the filter pad 101, through dye release pad 102 where it becomes coloured by the dye and into the dye receptor pad 100. Once the dyed saliva becomes visible on the dye receptor pad 100, the user is alerted that an adequate sample of saliva has been collected. The user then takes the test swab 70 and inserts it into the swab holder 16 of the test cartridge 10. As shown in FIG. 11, once the saliva collection pad 72 of the test swab 70 contacts the conjugate release pad 27 of the test cartridge, the tube 79 is prevented from being further inserted. Continued pressure on the outer tube 78 of the test swab 70 causes the outer tube 78 to move downwardly relative to the stationary tube 79 against the pressure of the spring 77 moving the elongate spike from the sampling position to the sample transferring position. As the outer tube 78 is depressed relative to the tube 79, the spike 64 moves downwardly in the bore of the tube 79 and pierces the capsule 68' causing the run fluid to move under gravitational force and capillary action through the dye release pad 102, dye receptor pad 100, filter pad 101 and onto the saliva collection pad 72 where it mixes with the saliva. It is then drawn onto the conjugate release pad 27 which is in intimate contact with the saliva collection pad 72. The swab holder 16 is provided at its upper end with resilient lips 104 which extend inwardly from the cylindrical swab holder 16. The lips 104 define a hole with a diameter which is slightly larger than that of the outer tube 78 but smaller than the diameter of the flange 76 on outer tube 78. The flange 76 is profiled such that there is a smooth change in diameter of the flange at the open end of the outer tube 78 and a more abrupt change at the upper extent of the flange 76 remote from the open end of the outer tube 78. Upon insertion of the outer tube 78 into the swab holder 16, the gradual change of diameter of the flange 76 forces the resilient lips of the swab holder apart allowing the outer tube 78 to pass into the swab holder 16. Once the outer tube 78 has been inserted to a point just beyond the extent of the flange 76, the lips of the swab holder 16 spring back to their original unstressed position and the outer tube 78 is effectively held in position relative to the swab holder 16 of test cartridge 10 preventing the test swab 70 from being accidentally removed from cartridge 10 and hence ensuring intimate contact of the saliva collection pad 72 and the conjugate release pad 27 for the duration of the test. The filter pad 101 may be used to prevent the dye from compromising the test results. Alternatively, a dye may be chosen which, although visible to the human eye, is invisible or nearly so, at the LED wavelength used by the screening device. The filter pad 101 may also limit the rate at which the run buffer is released from the pierced capsule 68' to the test cartridge 10, thereby improving the mixing of the saliva sample and the run fluid.

FIG. 12 shows a cut away side view of a third embodiment of a test swab which is suitable for use with a test cartridge. This embodiment of test swab 70 requires that a spike 64 is provided in the swab holder 16 of the test cartridge. As shown in FIG. 14 the spike 64 is attached to a spike holder 65 which in turn is attached to the swab holder 16. The spike 64 preferably has a cruciform cross-section as shown in FIG. 15. The test swab 70 comprises a saliva collection pad 72, a main tube 108, a run fluid chamber, or capsule, 68' and an indicator section. The indicator section comprises a capillary tube 110, a dye release pad 102 and a dye receptor pad 100. The saliva collection pad 72 is in communication with the open base of a main tube 108. The upper end of the main tube is also open. A penetrable gelatine capsule 68' filled with run fluid is located within the main tube 108 spaced from the saliva collection pad 72. Disposed to the side of the main tube 108 is a capillary tube 110. A small port 116 is provided in the wall of the main tube 110 a short distance from the saliva collection pad 72. The open lower end of the capillary tube 110 is attached to the main tube 108 at the port 116 and communicates with the main tube 108 via the port 116.

Provided around the periphery of the lower portion of the main tube 108 and capillary tube 110 is a guide 112 and insertion endstop 106. The end stop is spaced from the saliva collection pad 72 substantially the same distance as the distance from the centre of the capsule 68' to the saliva collection pad 72. The guide 112 and end stop 106 may extend around the whole periphery of the main and capillary tubes 108 and 110 or only partially around the periphery.

At the end of the capillary tube 110 remote from the port 116, a dye release pad 102 and dye receptor pad 100 are provided. The dye receptor pad 100 is positioned at the open end of the capillary tube 110 and is visible from the top and/or sides of the capillary tube 110. The dye release pad 102 is spaced from the dye receptor pad 100. In operation, as saliva is collected on the saliva collection pad 72, some of it is drawn up the capillary tube 110 by capillary action where it contacts the dye release pad 102. The saliva becomes dyed as it passes over the dye release pad 102 and as it travels further up the capillary tube 110 it contacts the dye receptor pad 100 which becomes visibly stained by the dye indicating that an adequate sample of saliva has been collected. The test swab 70 may then be removed from the mouth of the person being tested and inserted into the test cartridge 10. The guide 112 ensures that the test swab 70 is inserted optimally into the swab holder 16 and further ensures that the run fluid capsule 68' will be pierced by the spike 64 of the swab holder 16. The end stop 106 of the test swab 70 prevents the user from inserting the test swab 70 too far into the test cartridge and thus prevents the test cartridge from becoming damaged which may interfere with the proper running of the test. The user is alerted by the test stop hitting the periphery of the swab holder 16 that the test swab 70 is fully inserted and has been advanced far enough into the swab holder 16 for the spike 64 to have punctured the capsule 68' thereby releasing the run fluid which mixes with the saliva sample and is transported by gravitational and capillary action onto the conjugate release pad 27 of the test strip 23. The dye receptor pad 100 may be a cotton swab.

The guide 112 may be formed of simple projections with the diameter of the swab measured across the projections being slightly smaller than the diameter of the swab holder 16 such that when the swab is inserted into the swab holder 16 the guide 112 causes the swab to be centred in the swab holder 16. Alternatively the guide 112 may consist of an external thread arranged around the periphery of the main and capillary tubes 108 and 110 and co-operating with an internal thread provided on the bore of the swab holder 16. If the guide is provided by an external threaded portion then the end stop 106 may be omitted and the swab inserted until the end of the thread is reached determining the final position and pressure of the spike 64 on the capsule 68'. Other embodiments of the test swab may be provided.

Although described with reference to lateral flow immunoassay testing, the above described test swabs could be used to take a sample of saliva for agglutination testing. The difference being that instead of the saliva/run fluid mixture being drawn over a conjugate release pad and thereafter onto and along a nitrocellulose test strip, an agglutination test cartridge is provided.

The screening device may also be used to detect the results of agglutination tests. Agglutination tests are generally categorised into one of two categories depending on the size of the analyte whose presence is to be detected. The screening device may be used to determine the results of both agglutination categories.

In the first category, large analytes with multiple epitopes (binding sites) such as proteins can be detected. Coloured (or white) latex beads (microspheres or nanospheres) are coated with antibodies to the protein, suspended in an appropriate buffer solution, mixed with the sample under test and the mixture incubated. The presence of the antigen (ie the analyte whose concentration or presence in the sample is being tested and to which the antibodies are directed) in the sample causes multiple latex beads to bind together by bridging between two antibodies coated to different beads. Because the proteins (or other large molecule under test) are capable of binding with more than one antibody at a time due to their multiple epitopes and each latex particle has multiple antibodies coated to it, then complexes of beads are formed causing agglutination. Huge molecules, which are discernible to the naked eye, are formed by the large scale clumping. These molecules may be detected by the screening device and the relative concentration of the substance under test may be calculated, Use of the screening device allows the sensitivity of the test to be increased because individual pairs of bound latex beads (diners) can be detected by using imaging apparatus with sufficient optical magnification.

There are further advantages in using the screening device for the second category of agglutination reactions. In this second category, sometimes referred to as agglutination inhibition reactions, smaller analytes such as drugs can be detected. Coloured (or white) latex beads (or polystyrene beads or liposomes) which are irreversibly attached to drug molecules are manufactured. Free antibodies are mixed with the sample under test and then added to the coloured latex beads. If there are no drug molecules present in the sample, the antibodies bind with the coloured latex beads forming bridges between beads and agglutination which results in localised high concentrations of coloured latex beads which can then be detected. However, free drug molecules in the sample will compete for binding sites on the free antibodies with the drug bound latex beads. Hence, if a sample contains a drug being tested for, the drug molecules bind to the free antibodies which are not then free to bind with the latex beads, hence presence of the drug inhibits the agglutination which would otherwise occur. The absence, or reduction, of agglutination can be detected and the concentration of the drug in the sample may be calculated.

Other variants of these agglutination reactions such as using the device to monitor the rate of agglutination or the use of different types of particle or different reaction mechanisms will be obvious to those familiar with this field.

An embodiment of the screening device may also be used to screen agglutination reactions. In order to determine the results of an agglutination test, regions of (bio) chemical coagulation or agglutination (hereafter referred to as condensates) must be uniquely identified, counted, measured in area, colour and/or intensity and generally distinguished from one another. In the digitized image, the condensates of interest are generally larger than a single pixel and adjacent pixels belonging to the same condensate must be recognised as such. Distinct condensates must be differentiated. There are various sources of noise in the digitised image. Fixed pattern and random (statistical) distortions are introduced by the optical components. Spatial location and variations due to manufacturing tolerances of the components of the screening device also introduce random errors, Compensation for these errors is provided by the screening device. Correction for non-uniform illumination and differing imaging parameters (such as exposure and amplification) and variations in the concentrations of the test sample and reaction chemistry may also be corrected. Objects within the image which are too small, too large or of a particular shape may be disregarded. In the preferred embodiment, the instrument is hand held and powered by batteries. The image processing is capable of producing results accurately and rapidly using moderate computer processing and memory resources.

Figure 21:
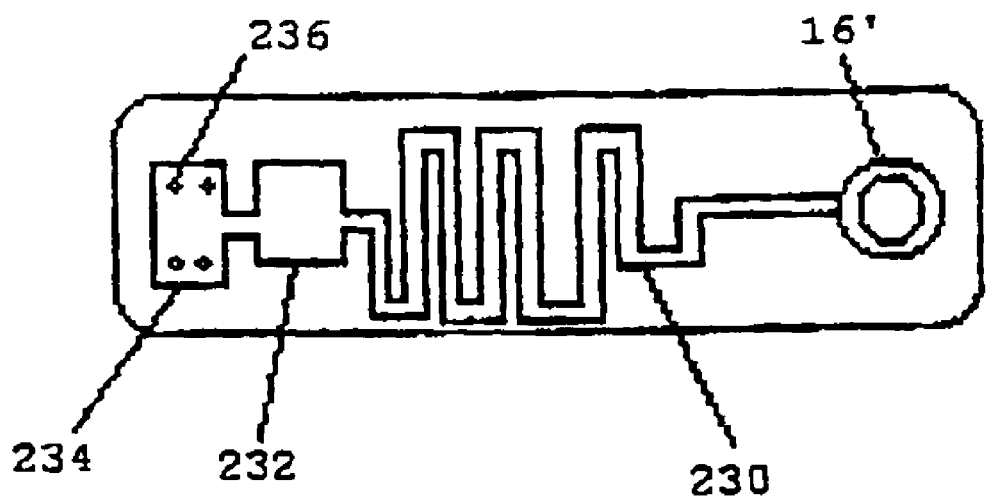
FIG. 21 is a plan view of a single reaction agglutination test cartridge.

FIG. 21 shows the plan view of a single reaction agglutination test cartridge. The test cartridge 10' is made of three sandwiched plastic layers. The middle layer defines the sides of the channel 230, the sides of the reaction chamber or chambers 232 and the sides of the overflow reservoir 234. The top layer defines holes forming venting holes 236 to the overflow reservoir 234 when the layers are assembled. The top layer also defines an entry port 16' into which the sample may be inserted. The entry port 16' communicates with the channel 230 provided in the middle layer. The bottom layer and top layer form the bottom and top respectively of the channel 230, reaction chamber 232 and overflow reservoir 234.

As described above, a sample of bodily fluid such as saliva is pre-processed by mixing with free antibodies to the drug under test and coloured latex beads which are irreversibly attached to the drug molecules under test, and the mixture applied to the test cartridge 10' using entry port 16'.

The sample is drawn from the entry port 16' along the channel 230. The channel is designed to have a length which allows time for any pre-processing reactions to occur. Once it has passed the length of the channel 230, the sample enters the reaction chamber 232 where agglutinates develop. An overflow reservoir 234 is provided in the test cartridge 10' and communicates with the reaction chamber 232. Once the reaction chamber is filled by the sample, excess sample moves to the overflow reservoir 234 which has venting holes 236 which are exposed to the atmosphere. The excess sample may therefore escape from the test cartridge 10' preventing pressure build-up inside the cartridge.

A window is provided in the top of the reaction chamber 232 and the window is illuminated by the screening device to detect the results of the agglutination reaction. Alternatively, the entire test cartridge 10' may be made from a plastics which is transparent to the wavelength of light used by the screening device.

Figure 22:
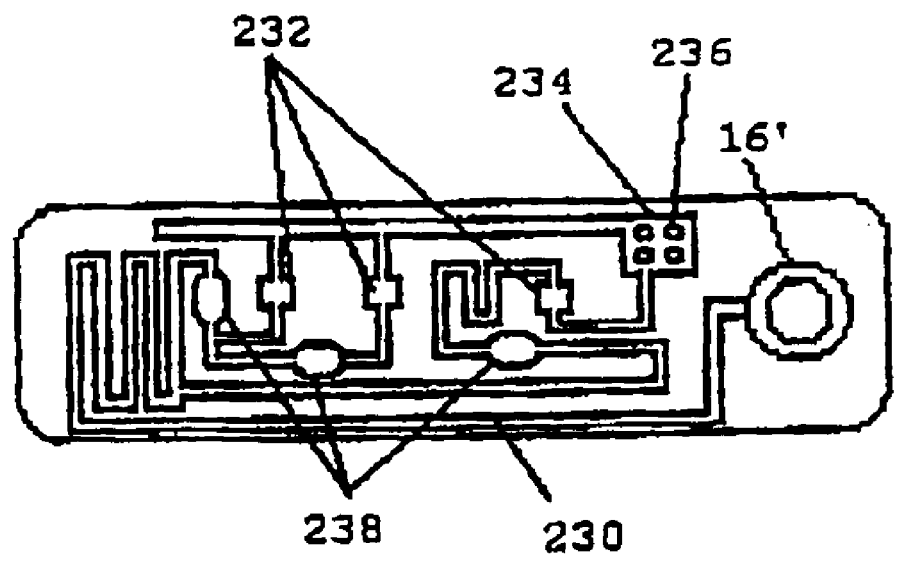
FIG. 22 is a plan view of a multiple reaction agglutination test cartridge.

FIG. 22 shows an agglutination test cartridge used to evaluate the presence or absence of multiple analytes. In addition to a plurality of reaction chambers 232, the test cartridge 10' provides a plurality of reactant chambers 238. Each reactant chamber 238 holds a supply of coloured latex beads irreversibly bound to molecules of the drug for which the test is being conducted. The reactants are held in an immobilised state for example by freeze drying. The saliva sample to be tested is mixed with free antibodies to the drug under test and supplied to the test cartridge 10' via the entry port 16'. The saliva/free antibody mix passes along the channels 230 into the reactant chambers 238 where it mixes with the coloured latex beads. The mixture then passes to the corresponding reaction chamber 232 where any agglutination reaction occurs. By using coloured latex beads bound to different drug molecules in each reactant chamber 238, the presence of a number of different drugs can be detected using a single test cartridge 16'. Each reaction chamber 232 communicates with the overflow reservoir 234 which has venting holes 236 exposed to the atmosphere. The reactant chambers 238 may be placed in series or in parallel as required by the test. In the embodiment of test cartridge 10' shown in FIG. 22, saliva/free antibody mixture is supplied directly to two of the three reactant chambers 238 with the third reactant chamber 238 being supplied with the mixture from one of other reactant chambers.

Alternatively, the reactant chamber 238 could hold a sample of free antibodies to the drug under test and the coloured latex beads irreversibly bound to the drug under test could be mixed with the saliva sample before the mixture is supplied to the entry port 16'. Three reaction chambers 232 are provided and the channel 230 bifurcates to allow entry of the sample to two of the three chambers 232. The third chamber is supplied with sample directly from one of the other chambers.

Windows are provided in the top of each of the reaction chambers and when processing the data using an embodiment of the screening device, preset data is provided to give the location of the different reaction chambers.

The image processing for agglutination reactions will now be described with reference to FIGS. 16–19.

Figure 16:
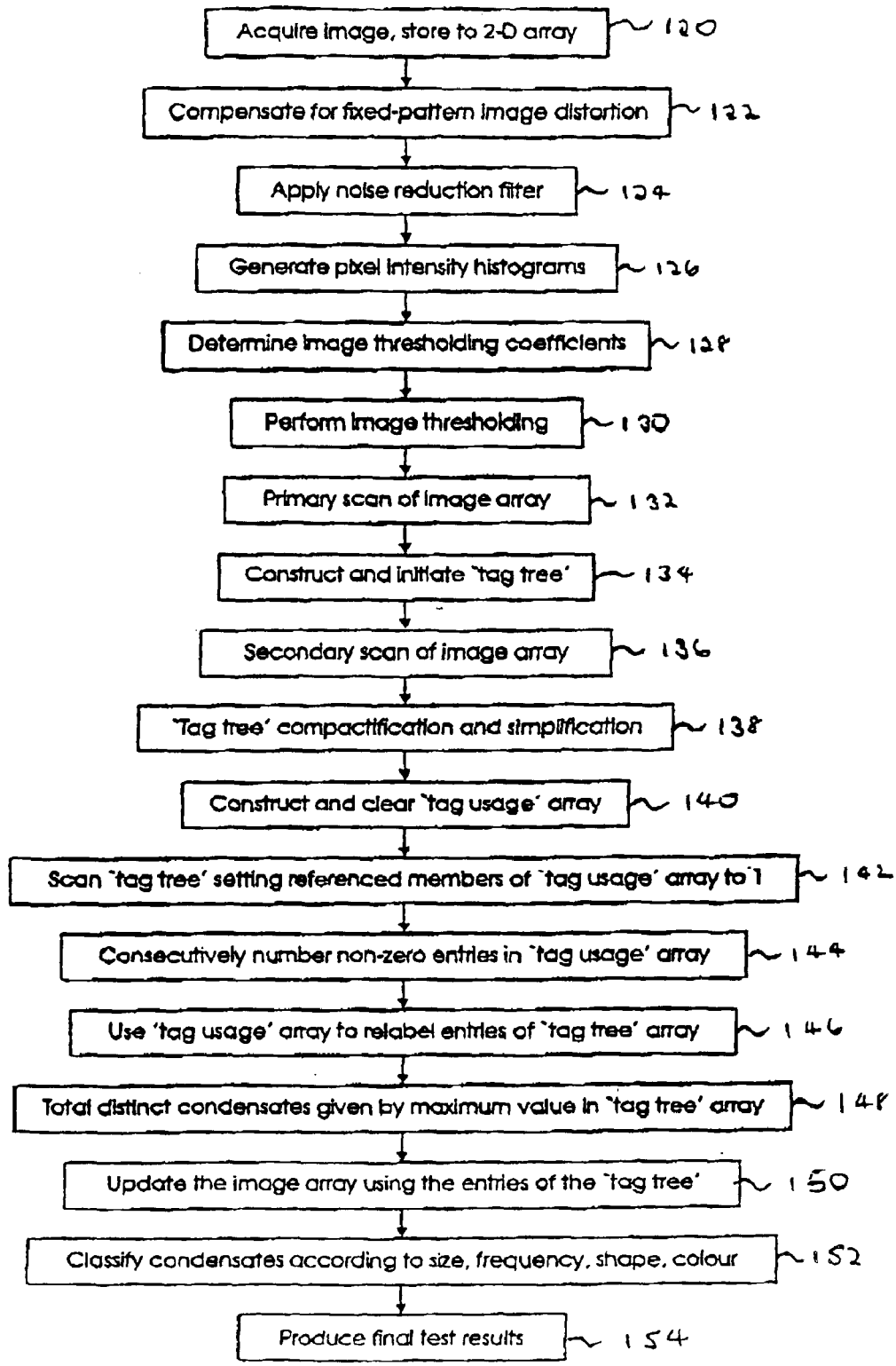
FIG. 16 is a flow chart showing the operation of a second embodiment of the screening device.

FIG. 16 shows a flow chart of the screening operation. The main difference between testing for an agglutination reaction and for an immunoassay test is that the CPU processes the digitized image in a different manner. The hardware of the screening device may be identical for screening immunoassay tests and agglutination reactions. Alternatively, the agglutination reaction may use a different size of test cartridge and the opening in the screening device may be adapted to accommodate the agglutination reaction test cartridge. An adaptor may be provided to allow two or more sizes or types of test cartridge to be used.

The image is acquired, digitised and the data stored to a 2-D array (120) by the imaging section of the screening device. The data array requires around 102 KB of memory (356×292 pixels×8 bits per pixel). The data processing can be conducted using a small amount of additional memory of say 8 KB thus eliminating the need for providing memory for a second array. The screening device is therefore provided with commonly available 128 KB static RAM. Fixed pattern image distortions are removed by applying various two-dimensional transformations to the data (122). These techniques can be used to remove tilt, trapezoidal, rotation, translation, pin-cushion (where the appearance of the image is distorted so that the centre of the image appears to have been pulled upwardly out of the plane of the image) or barrel distortion (where the appearance of the image is distorted so that the centre of the image appears to have been pushed downwardly through the plane of the image) of the image. Suitable 2–d transformations are simple mathematical equations for mapping the points of the distorted image to the corresponding points on the original object. If a continuous transformation is determined, it must be discretised for implementation in the processor. Alternatively, the transformation which maps the original image onto the distorted image may be estimated, in which case the inverse transformation must be calculated for application in the processor.

For agglutination test, the number of small condensates can be large and the accuracy of the result is limited by image resolution and distortion. It is therefore desirable to transform the image prior to any further processing to permit image scaling and the removal of distortion to be consistently achieved. By measuring for each image the location of the corners of the test window and the mid-points of the test window edges, an algorithm may be developed which calculates the mathematical transformation necessary to achieve a target window size, position, rotation and distortion.

Once any imaging distortions have been corrected, noise reduction (124) is performed by applying a 2-D low pass filter to the data. Once the data has been filtered, histograms of pixel intensities for the entire array are created (126). If necessary, histograms of pixel intensities of sub-sections of the array may be created. Using the pixel intensity histograms and knowledge of the underlying chemistry of the agglutination reaction, threshold intensities for sub-sections of the image are produced (128). For example if 20% of the image area is normally occupied by condensates, then the histogram can be used to determine the pixel intensity thresholds to divide the image sections into two portions, one approximately four times as large as the other. This information is test specific and is stored on preset data in the memory of the screening device. Once the thresholds have been determined, they are applied to the array to transform it into a monochrome 2–d array (130). Depending upon the chemistry involved, portions above (or below) the threshold value determined for each image section are interpreted as agglutination condensates or background regions, Condensate areas are then represented by negative integer values and the background regions by a zero value. Different image sub-sections may be represented by different negative integer values.

Figure 17:
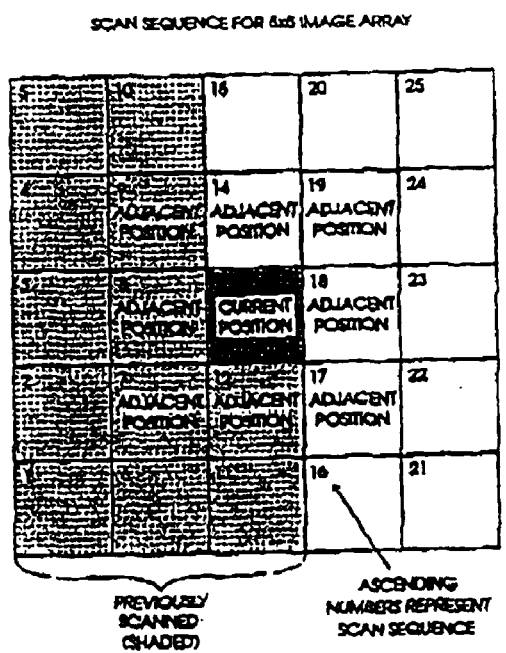
FIG. 17 is a schematic diagram showing the correspondence between the sequence of the element-wise processing of the monochrome data array and the position in the acquired image.
Figure 18:
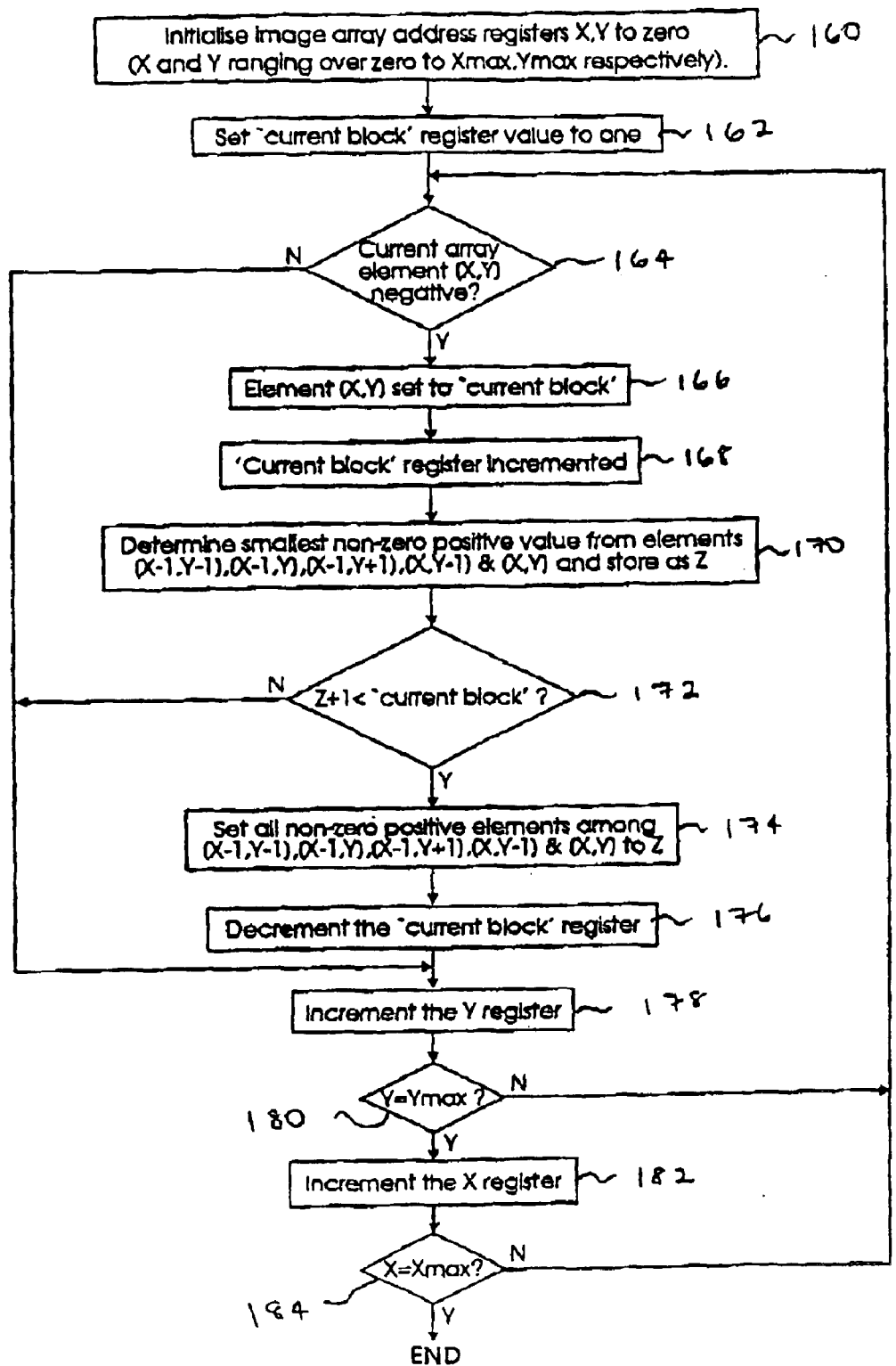
FIG. 18 is a flow chart showing the primary scan operation of FIG. 16.

The monochrome array is first processed to identify the background regions (zero valued entries) and a plurality of positively valued entries which closely approximate the location of the condensates (132). Flow charts for processing the monochrome array to identify background regions and condensates are shown in FIGS. 17 and 18. FIG. 18 is a flow chart showing the processing of the data during the scan. The image array address registers X and Y are initialised to zero (160). A current block register is initialised by setting the value to one (162). The monochrome array is sequentially processed. The order in which the array is processed is shown in FIG. 17.

FIG. 17 shows the sequence of the raster scan. Processing commences with the data which corresponds with the bottom lefthand corner of the image, works along one column of the agglutination test, moves to the adjacent row and starts processing the entries corresponding to the next column.

The elements are referenced by (X,Y) where $0 \leq X \leq X_{max}$ and $0 \leq Y \leq Y_{max}$ with X incrementing column-wise from left to right and Y incrementing row-wise from bottom to top. Elements in the array which store negative integers correspond to condensate areas.

As each element is accessed a check is made to determine whether the value stored in that element is negative (164). If the element is negative, the value of element is set to the value of the current block (166). The value of the current block is increased by one (168). The surrounding elements of the array which have already been scanned are identified. For example FIG. 17 shows as the current position element the central element. The adjacent previously scanned elements are those numbered 12, 7, 8 and 9. The values of these previously scanned adjacent elements are compared with each other and with the value of the current element. The smallest non-zero positive value of the current element and previously scanned adjacent elements is stored (170). Assuming that this value is stored as Z, the current block value is compared to the value of Z+1 (172). If the value of Z+1 is smaller than the value of the current block all non-zero positive elements among the previously scanned adjacent elements and the current element are tagged (174), that is the value stored in the element is set to the value Z, the current block is decreased by one (176) and the processor moves on to consider the next element in the array (180, 182 and 184). If the value of Z+1 is larger than or equal to the value of the current block then the current element pointer is incremented by one (178) and the processor moves on to consider the next element in the array. Processing continues until each element of the array has been processed in this manner (180, 182, 184).

Some of the condensates within the array will have been identified more than once by the above processing and areas of a single condensate may have different values or "tags". Where more than one tag relates to a single condensate, further processing to resolve the discrepancy is required. Tags which are equivalent, ie relate to the same condensate, must be identified and the information used to amend the array such that the same tag is used for each distinct condensate but different condensates are identified by different tags. A 1–d "tag tree" array is constructed (134). The length of the tag tree array is set by the value of the final current block from processing the monochrome array. For example, if the current block is say 5 after finishing the first processing, the tag tree array is a (1×5) array. The tag tree array is initialised such that each element references itself i.e. array(element)=element. Each tag (condensate label) is therefore mapped onto itself. By modifying the elements of the tag tree array, it is possible to identify equivalent tags. To do so, the processed monochrome array is processed a second time.

Figure 19:
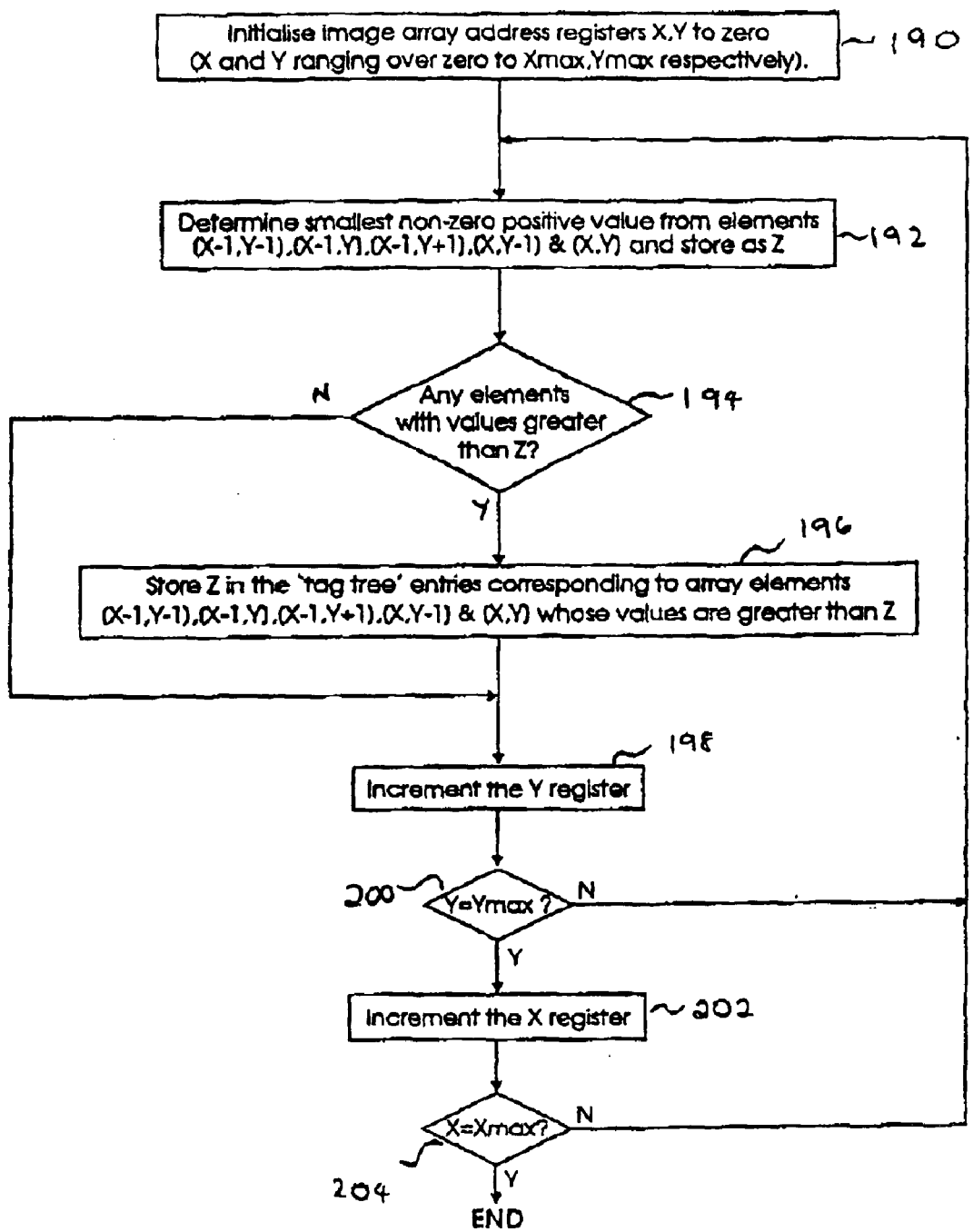
FIG. 19 is a flow chart showing the secondary scan operation of FIG. 16.

FIG. 19 shows a flow chart of the second processing operation. The processed monochrome array is processed element-wise in the same manner as described with reference to the first processing. For each element, the values of the current element and those previously processed array elements adjacent to the current element are compared (192). If any positive, non-zero entries are found, the lowest value is selected and stored in the tag tree array element corresponding to the higher value tag or tags (196). For example if the current element has a value 3, and the adjacent elements which have already been processed have the values 2, 3 and 4, then the value 2 is stored to the third and fourth tag tree elements. The equivalence between tags is thus recorded.

Figure 20:
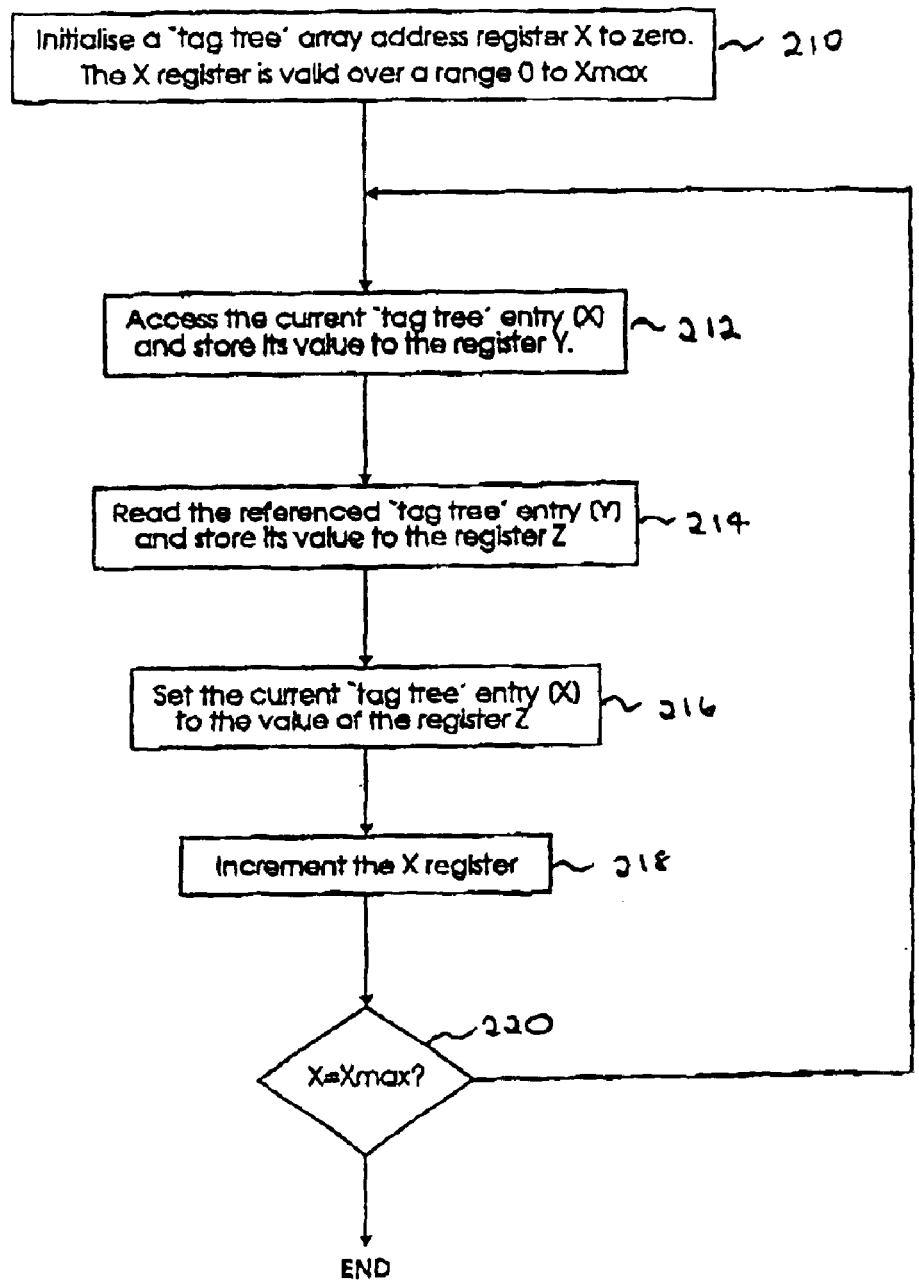
FIG. 20 is a flow chart showing the tag tree compaction and simplification operation of FIG. 16.

The elements of the 1–d tag tree are scanned from the first entry to the last and updated. FIG. 20 indicates the processing carried out. A tag tree address register X is initialised by setting all the entries to zero. X is valid over the range 0 to Xmax where Xmax is equal to one plus the number of elements in the tag tree array (210). The current tag tree entry is stored to a storage register Y (212). The element of the tag tree array corresponding to the value stored in storage register Y is accessed and its value stored in register Z (214). The current tag tree entry (X) is set to the value of register Z (216) and the X register incremented to process the next tag tree element (218) until all elements have been processed (220), For example for a 1–d tag tree containing a thousand entries numbered 1 to 1000 the initialised array is TREE [LEAF]=LEAF. After initial processing, it is possible for some entries (leaves) to be equivalent to others. For example, TREE[752]=329, TREE[839]=329, TREE[329]= 78 and TREE[78]=78. Entry 78 is equivalent to itself and is therefore a primary leaf, The remaining entries of this example can be related to the primary leaf by a branch [752,839]–[329]–[78] being the branch in this example. Scanning the tag tree decomposes the entries to leave all the entries TREE[752]=TREE[839]=TREE[329]=TREE[78]= 78. The entries of the tag tree are then limited to primary leaf values thereby eliminating branch values and setting all the entries of a branch to the same value.

When the scan is completed, only legitimately distinct "leaves" of the tree remain; the branches linking the leaves have been eliminated, The leaves are not necessarily contiguously arranged nor are they necessarily in ascending numerical order.

Referring now to FIG. 16, a tag usage array of identical length to the tag tree array is initialised by setting all the elements to zero (140). Each element of the updated tag tree is checked to see whether it is non-zero. For each non-zero value of the tag tree, the corresponding array element of the tag usage tree is set to one or any non-zero value (142). The current block register is then used to consecutively number the tag usage tree values. The current block register is set to one. In an element-wise fashion, each element of the tag usage tree is compared to zero and each time a non-zero entry is found, its value is set to the value of the current block register which is then incremented (144).

The tag tree is then updated once more using the tag usage array. The value of the current tag tree array element is used to reference the corresponding tag usage tree element. The value of the current tag tree array element is replaced by the value of the referenced tag usage tree element (146).

Once the tag tree has been updated, the elements are compared and the highest positive value indicates the number of distinct condensates detected in the original image (148). The processed monochrome array can be updated using the tag tree array (150). The array is processed element-wise as before and where the value stored for an element is positive and non-zero a check is made of the tag tree array to determine whether or not the value should be amended. Assuming the current element of the processed monochrome array is N and the value stored therein is 3, the $3^{rd}$ element of the tag tree array is accessed. The value stored in the $3^{rd}$ element of the tag tree array is then stored at the Nth element of the processed monochrome array. The twice processed monochrome array now represents the background regions denoted by zero-valued entries and contiguously numbered distinct condensates denoted by contiguous positive numbers. The condensates may be classified according to their size and relative frequency by counting the number of entries with the same positive non-zero values in the twice processed monochrome array (152).

The results obtained are used to determine whether the sample contained the analyte(s) being tested for (154). In the simplest case, the agglutination test measures just one analyte, For standard tests, high numbers of large agglutinates indicate a positive result whereas for inhibited agglutination reactions, this indicates a negative result. Depending on the properties of the noise reduction filter (124) and threshold determination (128), large numbers of small agglutinates may or may not be obtained. Therefore, the agglutinates may have to be categorised according to their size. This is achieved by performing a final image scan in which the number of times a particular tag occurs is recorded in a new data array. Agglutinates of size smaller than a given value are indicated by the new array having a value less than the threshold. These agglutinates may be disregarded in the results of the test.

In a manner similar to that of processing the results of agglutination tests, the screening device may be used to determine the outcome of precipitation reactions, reactions based on electrophoresis, immunoelectrophoresis, immunofixation electrophoresis, enzyme immunoassay and immunofluorescence, Any of these techniques may be adapted to allow the screening device to differentiate between the presence and absence of analyte in a patient sample by appropriate image processing. For certain reactions, the test may be designed to produce a colour change which can then be detected by the screening device. Kinematic analysis may be used both to determine the rate of change in colour and to determine the final test result. The screening device is capable of performing many kinds of kinematic analyses. Combination tests may be provided with the test bands for multiple analytes co-located on the test strip by ensuring the optical absorbency of each test is independent. The screening device may then differentiate between the independent test bands by scanning first with one optical wavelength and then with the next wavelength.

Channel-based reaction sequences may be designed such that intermediate reaction products deposited on the nitro-cellulose strip may be detected optically as the reaction progresses. Intermediate reaction products may allow for a reliable early warning of the test results before the test has been completed.

The latex beads may be bound to either analyte (drug) antibody or both. Bonds can form between two analytes via an intermediary, or carrier, molecule known as a protein bridge (for example polylysine). Reactions may be organised into one of two classes: competitive or non-competitive. These classes are akin to the distinction between agglutination and inhibition of agglutination reactions.

Kinematic analysis, where the rate of change in colour is determined, may also be undertaken by the screening device. The screening device may be provided with a plurality of illumination sources of differing wavelengths. Combination tests can be designed such that the test bands for multiple analytes are co-located but the optical absorbency is independent such that the screening device can differentiate between the results for the multiple analytes by illuminating the test strip with different wavelengths of light successively.

Instead of providing printed test zones spanning the entire width of the nitro-cellulose strip, it is possible to print an array of dots with each separate dot comprising a test zone for a different analyte. Where there are only a small number of analytes to be tested, the separate dots and the control band or dots may be printed closer to the conjugate release pad to reduce the run time of the test.

It is also possible that an assay test is designed whereby intermediate reaction products are deposited during the reaction process. These reaction products may be detectable prior to the completion of the test and in certain circumstances, it is desirable to provide an early output where the results of the test can be reliably reported using the intermediate reaction products.

With respect to the above description, it is to be realized that equivalent apparatus and methods are deemed readily apparent to one skilled in the art, and all equivalent apparatus and methods to those illustrated in the drawings and described in the specification are intended to be encompassed by the present invention. Therefore, the foregoing is considered as illustrative only of the principles of the invention. Further, since numerous modifications and changes will readily occur to those to skilled in the art, it is not desired to limit the invention to the exact construction and operation shown and described, and accordingly, all suitable modifications and equivalents may be resorted to, falling within the scope of the invention.

For example, in alternative embodiments of the invention, the sample to be tested could include urine, serum, plasma, ocular fluid or filtered whole blood. Suitable filtering systems for whole blood could be incorporated into the cartridge. The screening device could also used in other areas of immunodiagnostics. For example, the screening device could be used to analyse the concentration of tumour markers in the blood samples of patients undergoing treatment for cancer. The screening device could also be adapted for use to measure the levels of hormone, or therapeutic drug present in a sample or to test for bacteria, viruses or other microorganisms present in a variety of sample types. Alternatively the screening device could be adapted to screen samples for allergies.

It should be noted that the features described by reference to particular figures and at different points of the description may be used in combinations other than those particularly described or shown. All such modifications are encompassed within the scope of the invention as set forth in the following claims.

What is claimed is:

1. A screening arrangement to test for presence of a compound in a fluid specimen, comprising:
    a support cartridge having at least one elongate immunoassay test strip mounted thereon to which a fluid specimen is applied, the test strip including a test membrane having at least one test zone that changes reflectivity as a function of the amount of the compound in the specimen, at least one control zone that changes reflectivity upon contact with the specimen, and a background zone between the test and control zones;

a screening device for mounting thereon the support cartridge and the test strip associated therewith to test for the presence of the compound when the fluid specimen is applied to the test strip;

said screening device being portable, and including:

a receiving bracket removably mounting the support cartridge and the test strip carried thereon in a predefined stationary testing position so that an exposed surface of the membrane faces generally upwardly, a photosensitive detector assembly stationarily interconnected to and positioned adjacent said receiving bracket and directed toward a region directly above the upper surface of the test strip for receiving light reflected by the test membrane, said photosensitive detector assembly generating output signals representative of the concentration of light reflected by the test, control and background zones of the test membrane, a mirror arrangement interconnected to and positioned adjacent said receiving bracket and oriented for receiving light reflected from the test membrane and redirecting it to the photosensitive detector assembly, a processor to receive the output signals from the photosensitive detector assembly and configured (1) to evaluate the concentration of light reflected from the control zone to determine if the assay test has been successfully run and (2) to evaluate the concentration of light reflected from the test zone and to generate output data representative of the presence of the compound in the specimen, a visual display disposed adjacent one side of the screening device and connected to the processor for receiving the output data, and means for supplying d.c. voltage to the portable screening device for supplying power for operation thereof;

whereby said portable screening device, in conjunction with the support cartridge bearing the test strip thereon, is utilized for testing the fluid specimen while providing flexibility with respect to its handling and location of use.

2. The screening arrangement according to claim 1, wherein:

said processor is connected to said display and is configured to control the display so that if the test is not successful, said processor causes said display to generate a message indicating the test is not successful, and if the test is successful said processor causes said display to generate a message indicating the presence/absence of the compound in the specimen.

3. The screening arrangement according to claim 1, wherein the screening device mounts therein a visual indicator light for indicating when a test is in process and has been completed.

4. The screening arrangement according to claim 1, wherein the support cartridge has a swab-receiving structure fixedly associated with one end thereof and providing fluid communication with the test strip so that, when a swab having the fluid specimen thereon is inserted into the swab-receiving structure, the specimen is placed in fluid communication with the test strip; and said swab-supporting structure and the swab engaged therewith being positioned sidewardly from the upper exposed surface of the test membrane so as to not interfere with the test strip when the support cartridge is mounted on the receiving bracket.

5. The screening arrangement according to claim 1, wherein said screening device includes a position detector positioned adjacent the receiving bracket for sensing when the support cartridge is properly supported and positioned on the receiving bracket for permitting initiating of a test.

6. The screening arrangement according to claim 1, wherein the means for supplying d.c. voltage to the screening device includes a battery arrangement carried therewith.

7. The screening arrangement according to claim 6, wherein the display is oriented vertically adjacent an opposite side of the screening device, and wherein the photosensitive detector assembly, the processor and the battery arrangement are all positioned generally between the display arid the receiving bracket.

8. The screening arrangement according to claim 1, wherein the receiving bracket defines a generally horizontally open guide track which cooperates with the support cartridge so as to enable the support cartridge to be horizontally slidably inserted into the guide track for disposition in said predetermined position.

9. The screening arrangement according to claim 1, wherein the screening device has a maximum weight of approximately 300 grams.

10. The screening arrangement according to claim 1, wherein the screening device includes a plurality of lights disposed above the receiving bracket to individually emit light downwardly toward the exposed upper surface of the test membrane, each said light emitting a different light frequency.

11. The screening arrangement according to claim 1, wherein the processor is configured to evaluate the concentration of light reflected from the control zone relative to the concentration of light reflected from the adjacent background zone to determine if the assay test has been successfully run, and to evaluate the concentration of light reflected from the test zone relative to the concentration of light reflected from the adjacent background zone to generate data representative of the compound in the specimen.

12. The screening arrangement according to claim 1, wherein the screening device is a portable unitized assembly.

13. The screening arrangement according to claim 1, wherein the screening arrangement includes a light arrangement disposed above the receiving bracket to emit light downwardly toward the exposed upper surface of the test membrane.

* * * * *